(12) United States Patent
Shudo et al.

(10) Patent No.: US 11,925,464 B2
(45) Date of Patent: Mar. 12, 2024

(54) EVALUATION APPARATUS, EVALUATION METHOD, AND NON-TRANSITORY STORAGE MEDIUM

(71) Applicant: JVCKENWOOD Corporation, Yokohama (JP)

(72) Inventors: Katsuyuki Shudo, Yokohama (JP); Makoto Kito, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 808 days.

(21) Appl. No.: 17/030,441

(22) Filed: Sep. 24, 2020

(65) Prior Publication Data
US 2021/0007653 A1 Jan. 14, 2021

Related U.S. Application Data

(63) Continuation of application No. PCT/JP2019/009540, filed on Mar. 8, 2019.

(30) Foreign Application Priority Data

Mar. 26, 2018 (JP) .................................. 2018-057997
Jan. 28, 2019 (JP) .................................. 2019-012344

(51) Int. Cl.
*A61B 5/16* (2006.01)
*A61B 5/00* (2006.01)

(52) U.S. Cl.
CPC ............ *A61B 5/163* (2017.08); *A61B 5/4064* (2013.01); *A61B 5/4088* (2013.01); *A61B 5/7435* (2013.01)

(58) Field of Classification Search
CPC ..... A61B 5/163; A61B 5/4064; A61B 5/7435; A61B 5/4088
See application file for complete search history.

(56) References Cited

U.S. PATENT DOCUMENTS

2016/0106354 A1 4/2016 Shudo et al.
2017/0188930 A1 7/2017 Lahvis
2017/0224210 A1 8/2017 Mori et al.

FOREIGN PATENT DOCUMENTS

EP 3613334 2/2020
JP 2010-132406 6/2010
(Continued)

OTHER PUBLICATIONS

Extended European Search Report for European Patent Application No. 19776199.2 dated Mar. 30, 2021.
(Continued)

*Primary Examiner* — Eric F Winakur
(74) *Attorney, Agent, or Firm* — Amin, Turocy & Watson, LLP

(57) ABSTRACT

An evaluation apparatus includes: a display screen; a gaze point detecting unit that detects a position of a gaze point of a subject observing the display screen; a display control unit that causes the display screen to display an image including a specific object and a comparison object different from the specific object; an area setting unit that sets a specific area corresponding to the specific object and a comparison area corresponding to the comparison object; a determining unit that, based on the position of the gaze point, determines whether the gaze point is present in the specific area and the comparison area during a period in which the image is displayed; a calculating unit that calculates gaze point data based on the determination result of the determining unit; and an evaluating unit that obtains evaluation data of the subject based on the gaze point data.

5 Claims, 20 Drawing Sheets

(56) References Cited

FOREIGN PATENT DOCUMENTS

| | | |
|---|---|---|
| JP | 2011-37623 | 2/2011 |
| JP | 2011-083403 | 4/2011 |
| JP | 2015-177953 | 10/2015 |
| JP | 2016-171849 | 9/2016 |
| WO | 12016/052646 | 4/2016 |

OTHER PUBLICATIONS

International Search Report and Written Opinion for International Application No. PCT/JP2019/009540 dated May 21, 2019, 12 pages.

EVALUATION APPARATUS, EVALUATION METHOD, AND NON-TRANSITORY STORAGE MEDIUM

CROSS-REFERENCE TO RELATED APPLICATIONS

This application is a Continuation of PCT International Application No. PCT/JP2019/009540 filed in Japan on Mar. 8, 2019, which claims priority to and incorporates by references the entire contents of Japanese Patent Application No. 2018-057997 filed in Japan on Mar. 26, 2018 and Japanese Patent Application No. 2019-012344 filed in Japan on Jan. 28, 2019.

BACKGROUND

1. Technical Field

The present disclosure relates to an evaluation apparatus, an evaluation method, and a non-transitory storage medium.

2. Description of the Related Art

It is said that there has been a recent increasing trend in cognitive dysfunction and brain dysfunction such as dementia, and there is a need to find cognitive dysfunction and brain dysfunction at an early stage and quantitatively evaluate the severity of symptoms. It is known that the symptoms of cognitive dysfunction and brain dysfunction affect the memory ability. Therefore, the subject is evaluated based on the memory ability of the subject. For example, there is a disclosed apparatus that displays a plurality of types of numbers, prompts the subject to add the numbers and find an answer, and checks the answer given by the subject (for example, see Japanese Laid-Open Patent Application No. 2011-083403).

However, the method in Patent literature 1 or the like provides a simple answer selection mode and has difficulty in verification including the accidentalness and therefore it is difficult to obtain a high evaluation accuracy. Thus, there is demand for high-accuracy evaluation of cognitive dysfunction and brain dysfunction.

SUMMARY

According to an aspect, an evaluation apparatus includes: a display screen; a gaze point detecting unit configured to detect a position of a gaze point of a subject observing the display screen; a display control unit configured to cause the display screen to display an image including a specific object and a comparison object different from the specific object; an area setting unit configured to set a specific area corresponding to the specific object and a comparison area corresponding to the comparison object; a determining unit configured to determine, based on the position of the gaze point, whether the gaze point is present in the specific area and the comparison area during a display period in which the image is displayed; a calculating unit configured to calculate gaze point data based on a determination result of the determining unit; and an evaluating unit configured to obtain evaluation data of the subject based on the gaze point data. The display control unit is configured to perform a first display operation to change a display form of the specific object during a period in which the specific object and the comparison object are displayed on the display screen and then performs a second display operation to display the specific object and the comparison object on the display screen. The display control unit is configured to cause instruction to be displayed so as to prompt the subject to memorize the object that changes in the display form in the first display operation.

According to an aspect, an evaluation method includes: displaying an image on a display screen; detecting a position of a gaze point of a subject observing the display screen; causing the display screen to display the image including a specific object and a comparison object different from the specific object; setting a specific area corresponding to the specific object and a comparison area corresponding to the comparison object; determining, based on the position of the gaze point, whether the gaze point is present in the specific area and the comparison area during a display period in which the display screen displays the image; calculating gaze point data during the display period based on the determination result; obtaining evaluation data of the subject based on the gaze point data; performing a first display operation to change a display form of the specific object during a period in which the specific object and the comparison object are displayed on the display screen, and then performing a second display operation to display the specific object and the comparison object on the display screen; and causing instruction to be displayed so as to prompt the subject to memorize the object that changes in the display form in the first display operation.

According to an aspect, a non-transitory storage medium stores a computer program configured to cause a computer to execute: a process of displaying an image on a display screen; a process of detecting a position of a gaze point of a subject observing the display screen; a process of causing the display screen to display the image including a specific object and a comparison object different from the specific object; a process of setting a specific area corresponding to the specific object and a comparison area corresponding to the comparison object; a process of determining, based on the position of the gaze point, whether the gaze point is present in the specific area and the comparison area during a display period in which the display screen displays the image; a process of calculating gaze point data during the display period based on the determination result; a process of obtaining evaluation data of the subject based on the gaze point data; a process of performing a first display operation to change a display form of the specific object during a period in which the specific object and the comparison object are displayed on the display screen, and then performing a second display operation to display the specific object and the comparison object on the display screen; and a process of causing instruction to be displayed so as to prompt the subject to memorize the object that changes in the display form in the first display operation.

DETAILED DESCRIPTION

An embodiment of an evaluation apparatus, an evaluation method, and an evaluation program according to the present disclosure is described below with reference to the drawings. It should be noted that the present disclosure is not limited to the embodiment. Furthermore, the components in the following embodiment include the one that may be easily replaced by those skilled in the art or substantially the same one.

In the following description, the three-dimensional global coordinate system is set to describe the positional relationship between components. The direction parallel to a first axis of a predetermined plane is an X-axis direction, the direction parallel to a second axis of the predetermined plane perpendicular to the first axis is a Y-axis direction, and the direction parallel to a third axis perpendicular to the first axis and the second axis is a Z-axis direction. The predetermined surface includes an XY plane.

(Line-of-Sight Detection Device)

Figure 1:
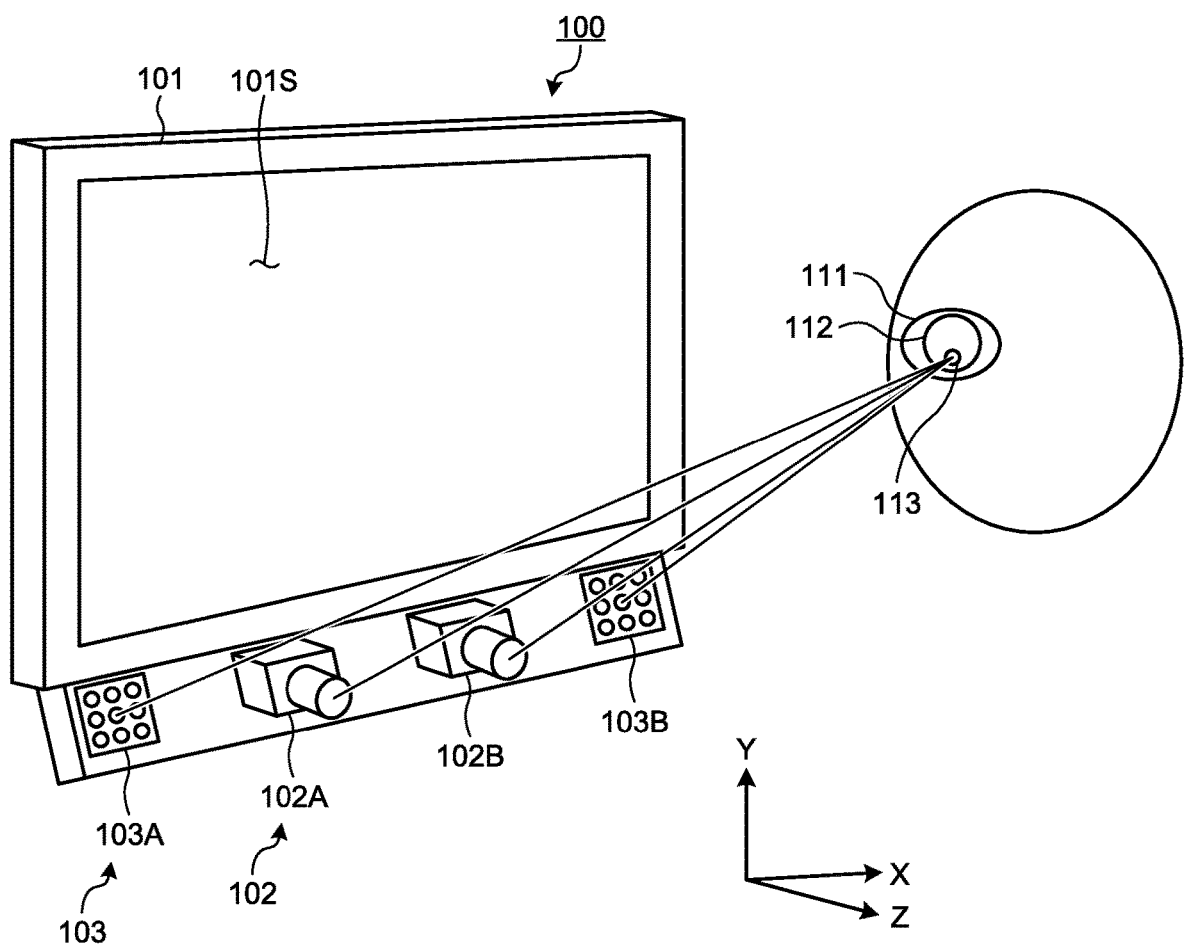
FIG. 1 is a perspective view schematically illustrating an example of a line-of-sight detection device according to an embodiment.

FIG. 1 is a perspective view schematically illustrating an example of a line-of-sight detection device 100 according to a first embodiment. The line-of-sight detection device 100 is used as an evaluation apparatus that evaluates cognitive dysfunction and brain dysfunction such as dementia. As illustrated in FIG. 1, the line-of-sight detection device 100 includes a display device 101, a stereo camera device 102, and a lighting device 103.

The display device 101 includes a flat panel display, such as a liquid crystal display (liquid crystal display: LCD) or an organic EL display (organic electroluminescence display: OLED). According to the embodiment, the display device 101 includes a display screen 101S. The display screen 101S displays an image. According to the embodiment, the display screen 101S displays, for example, the indicator for evaluating the visual function of the subject. The display screen 101S is substantially parallel to the XY-plane. The X-axis direction is the horizontal direction of the display screen 101S, the Y-axis direction is the vertical direction of the display screen 101S, and the Z-axis direction is the depth direction perpendicular to the display screen 101S.

The stereo camera device 102 includes a first camera 102A and a second camera 102B. The stereo camera device 102 is disposed below the display screen 101S of the display device 101. The first camera 102A and the second camera 102B are arranged in the X-axis direction. The first camera 102A is disposed in the −X direction with respect to the second camera 102B. Each of the first camera 102A and the second camera 102B includes an infrared camera including an optical system capable of transmitting near-infrared light having a wavelength of, for example, 850 [nm] and an imaging sensor capable of receiving the near-infrared light.

The lighting device 103 includes a first light source 103A and a second light source 103B. The lighting device 103 is disposed under the display screen 101S of the display device 101. The first light source 103A and the second light source 103B are arranged in the X-axis direction. The first light source 103A is disposed in the −X direction with respect to the first camera 102A. The second light source 103B is disposed in the +X direction with respect to the second camera 102B. Each of the first light source 103A and the second light source 103B includes an LED (light emitting diode) light source so as to emit near-infrared light having a wavelength of, for example, 850 [nm]. The first light source 103A and the second light source 103B may be disposed between the first camera 102A and the second camera 102B.

The lighting device 103 emits near-infrared light, which is detection light, to illuminate an eyeball 111 of the subject. The stereo camera device 102 captures part of the eyeball 111 (hereinafter, this is also referred to as "eyeball") with the second camera 102B when the eyeball 111 is irradiated with the detection light emitted from the first light source 103A, and captures the eyeball 111 with the first camera 102A when the eyeball 111 is irradiated with the detection light emitted from the second light source 103B.

At least one of the first camera 102A and the second camera 102B outputs a frame synchronization signal. The first light source 103A and the second light source 103B emit the detection light based on a frame synchronization signal. The first camera 102A captures the image data of the eyeball 111 when the eyeball 111 is irradiated with the detection light emitted from the second light source 103B. The second camera 102B captures the image data of the eyeball 111 when the eyeball 111 is irradiated with the detection light emitted from the first light source 103A.

When the eyeball 111 is irradiated with the detection light, part of the detection light is reflected by a pupil 112, and the light from the pupil 112 enters the stereo camera device 102. When the eyeball 111 is irradiated with the detection light, a corneal reflection image 113, which is a virtual image in the cornea, is formed in the eyeball 111, and the light from the corneal reflection image 113 enters the stereo camera device 102.

By appropriately setting the relative positions of the first camera 102A, the second camera 102B, the first light source 103A, and the second light source 103B, the intensity of light entering the stereo camera device 102 from the pupil 112 is decreased, and the intensity of light entering the stereo camera device 102 from the corneal reflection image 113 is increased. That is, the image of the pupil 112 captured by the stereo camera device 102 has a low luminance, and the image of the corneal reflection image 113 has a high luminance. The stereo camera device 102 may detect the position of the pupil 112 and the position of the corneal reflection image 113 based on the luminance of the captured images.

Figure 2:
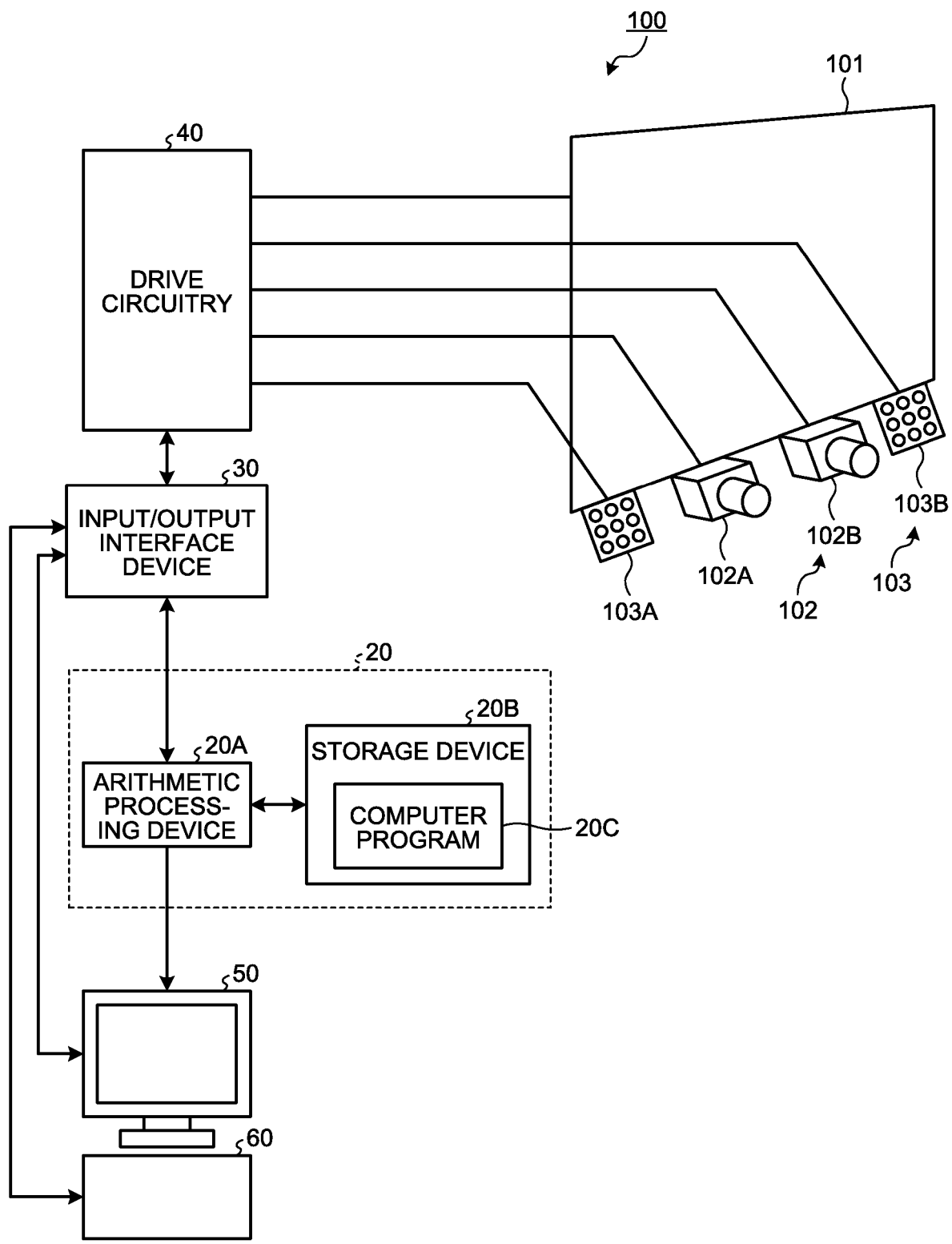
FIG. 2 is a diagram illustrating an example of the hardware configuration of the line-of-sight detection device according to the embodiment.

FIG. 2 is a diagram illustrating an example of the hardware configuration of the line-of-sight detection device 100 according to the embodiment. As illustrated in FIG. 2, the line-of-sight detection device 100 includes the display device 101, the stereo camera device 102, the lighting device 103, a computer system 20, an input/output interface device 30, a drive circuitry 40, an output device 50, and an input device 60.

The computer system 20, the drive circuitry 40, the output device 50, and the input device 60 perform data communications via the input/output interface device 30. The computer system 20 includes an arithmetic processing device 20A and a storage device 20B. The arithmetic processing device 20A includes a microprocessor, such as a central processing unit (CPU). The storage device 20B includes a memory, such as a read only memory (ROM) and a random access memory (RAM), or a storage. The arithmetic processing device 20A performs arithmetic processing in accordance with a computer program 20C stored in the storage device 20B.

The drive circuitry 40 generates drive signals and outputs it to the display device 101, the stereo camera device 102, and the lighting device 103. The drive circuitry 40 supplies the image data of the eyeball 111 captured by the stereo camera device 102 to the computer system 20 via the input/output interface device 30.

The output device 50 includes a display device, such as a flat panel display. The output device 50 may include a printing device. The input device 60 is operated and thus generates input data. The input device 60 includes a keyboard or a mouse for a computer system. The input device 60 may include a touch sensor provided on the display screen of the output device 50 that is a display device.

In the embodiment, the display device 101 and the computer system 20 are separate devices. The display device 101 and the computer system 20 may be integrated with each other. For example, when the line-of-sight detection device 100 includes a tablet personal computer, the tablet personal computer may include the computer system 20, the input/output interface device 30, the drive circuitry 40, and the display device 101.

Figure 3:
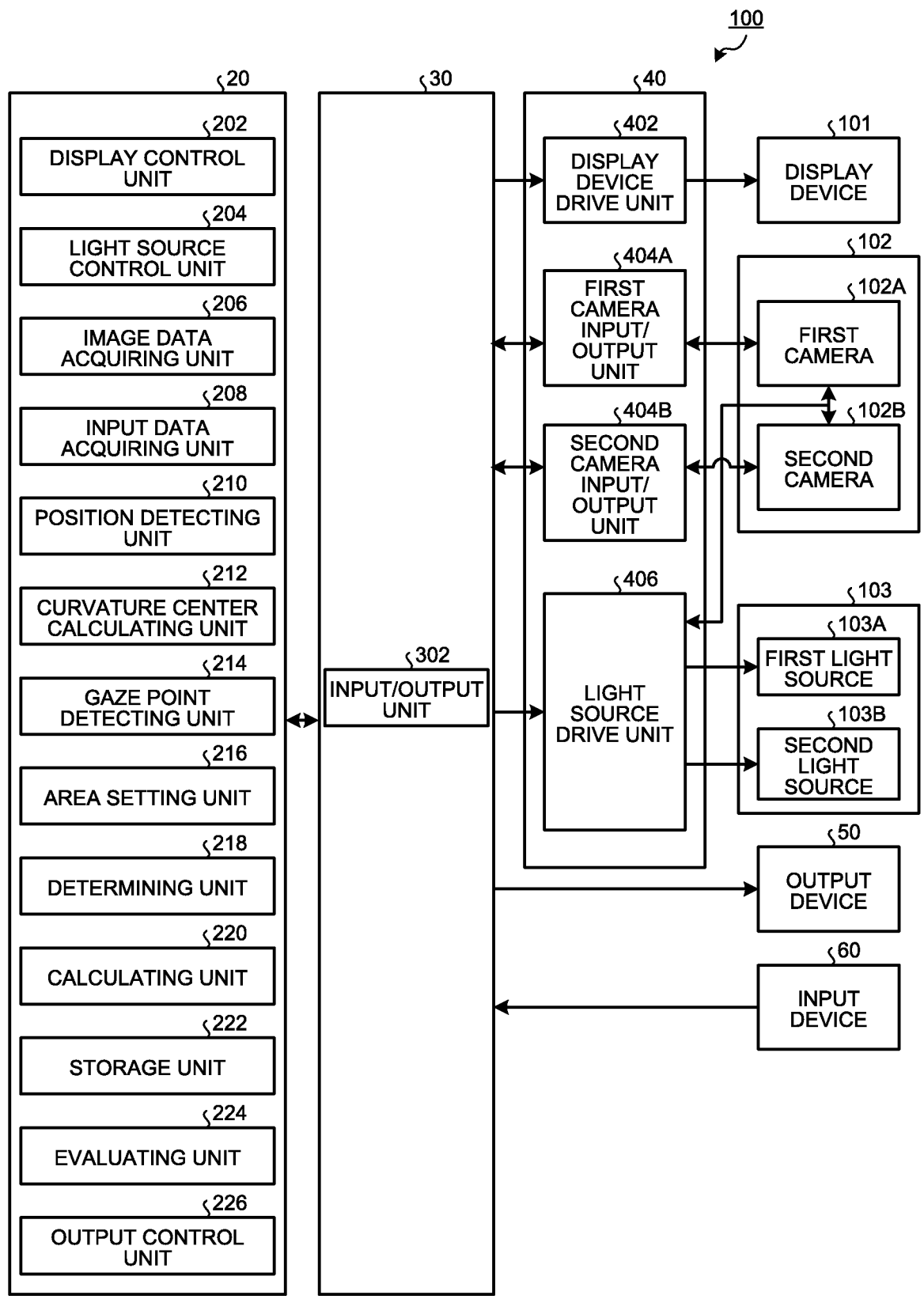
FIG. 3 is a functional block diagram illustrating an example of the line-of-sight detection device according to the embodiment.

FIG. 3 is a functional block diagram illustrating an example of the line-of-sight detection device 100 according to the embodiment. As illustrated in FIG. 3, the input/output interface device 30 includes an input/output unit 302. The drive circuitry 40 includes: a display device drive unit 402 that generates a drive signal for driving the display device 101 and outputs it to the display device 101; a first camera input/output unit 404A that generates a drive signal for driving the first camera 102A and outputs it to the first camera 102A; a second camera input/output unit 404B that generates a drive signal for driving the second camera 102B and outputs it to the second camera 102B; and a light source drive unit 406 that generates a drive signal for driving the first light source 103A and the second light source 103B and outputs it to the first light source 103A and the second light source 103B. The first camera input/output unit 404A supplies the image data of the eyeball 111 captured by the first camera 102A to the computer system 20 via the input/output unit 302. The second camera input/output unit 404B supplies the image data of the eyeball 111 captured by the second camera 102B to the computer system 20 via the input/output unit 302.

The computer system 20 controls the line-of-sight detection device 100. The computer system 20 includes a display control unit 202, a light source control unit 204, an image data acquiring unit 206, an input data acquiring unit 208, a position detecting unit 210, a curvature center calculating unit 212, a gaze point detecting unit 214, an area setting unit 216, a determining unit 218, a calculating unit 220, a storage unit 222, an evaluating unit 224, and an output control unit 226. The functions of the computer system 20 are implemented by the arithmetic processing device 20A and the storage device 20B.

The display control unit 202 performs a display operation including a first display operation to display a specific object on the display screen 101S and a second display operation to display, on the display screen 101S, the specific object and a plurality of comparison objects different from the specific object after performing the first display operation. The specific object is an object to be memorized by the subject. The comparison objects are the objects to be displayed on the display screen 101S side by side with the specific object so as to prompt the subject to find the specific object. The display control unit 202 may cause the display screen 101S to display the indication for instructing the subject to memorize the specific object displayed during the first display operation. The display control unit 202 may cause the display screen 101S to display the indication for instructing the subject to gaze at the specific object among the specific object and the comparison objects displayed during the second display operation.

The light source control unit 204 controls the light source drive unit 406 so as to control the operating states of the first light source 103A and the second light source 103B. The light source control unit 204 controls the first light source 103A and the second light source 103B such that the first light source 103A and the second light source 103B emit detection light at different timings.

The image data acquiring unit 206 acquires the image data of the eyeball 111 of the subject captured by the stereo camera device 102 including the first camera 102A and the second camera 102B, from the stereo camera device 102 via the input/output unit 302.

The input data acquiring unit 208 acquires the input data generated by the operation performed on the input device 60, from the input device 60 via the input/output unit 302.

The position detecting unit 210 detects the positional data of the pupil center based on the image data of the eyeball 111 acquired by the image data acquiring unit 206. The position detecting unit 210 detects the positional data of the corneal reflection center based on the image data of the eyeball 111 acquired by the image data acquiring unit 206. The pupil center is the center of the pupil 112. The corneal reflection center is the center of the corneal reflection image 113. The position detecting unit 210 detects the positional data of the pupil center and the positional data of the corneal reflection center with regard to each of the left and right eyeballs 111 of the subject.

The curvature center calculating unit 212 calculates the positional data of the corneal curvature center of the eyeball 111 based on the image data of the eyeball 111 acquired by the image data acquiring unit 206.

The gaze point detecting unit 214 detects the positional data of the gaze point of the subject based on the image data of the eyeball 111 acquired by the image data acquiring unit 206. In the embodiment, the positional data of the gaze point is a positional data of the intersection point between the eye vector of the subject defined in the three-dimensional global coordinate system and the display screen 101S of the display device 101. The gaze point detecting unit 214 detects the eye vector of each of the left and right eyeballs 111 of the subject based on the positional data of the pupil center and the positional data of the corneal curvature center acquired from the image data of the eyeballs 111. After the eye vector is detected, the gaze point detecting unit 214 detects the positional data of the gaze point indicating the intersection point between the eye vector and the display screen 101S.

The area setting unit 216 sets a specific area corresponding to the specific object and comparison areas corresponding to the comparison objects on the display screen 101S of the display device 101 during the display period in which the second display operation is performed.

The determining unit 218 determines whether the gaze point is present in the specific area and the comparison areas based on the positional data of the gaze point during the display period in which the second display operation is performed and outputs the determination data. The determining unit 218 determines whether the gaze point is present in the specific area and the comparison area, for example, at regular time intervals. The regular time interval may be, for example, the cycle (e.g., every 20 [msec]) of frame synchronization signals output from the first camera 102A and the second camera 102B.

Based on the determination data from the determining unit 218, the calculating unit 220 calculates movement progress data (referred to as gaze point data in some cases) indicating the progress of movement of the gaze point during the display period. The movement progress data includes: reaching time data indicating a period of time from when the display period starts to when the gaze point first reaches the specific area; movement frequency data indicating the number of times that the position of the gaze point moves among the comparison areas before the gaze point first reaches the specific area; presence time data indicating a presence time during which the gaze point is present in the specific area or the comparison areas in the display period; and final area data indicating a final area in which the gaze point is finally present among the specific area and the comparison areas in the display time.

The calculating unit 220 includes a management timer for managing the reproduction time of a video; and a detection timer T1 for detecting the elapsed time after a video is displayed on the display screen 101S. The calculating unit 220 includes a counter for counting the number of times it is determined that the gaze point is present in the specific area.

The evaluating unit 224 obtains evaluation data of the subject based on the movement progress data. The evaluation data is data for making an evaluation as to whether the subject is able to gaze at the specific object displayed on the display screen 101S during the display operation.

The storage unit 222 stores the determination data, the movement progress data (the presence time data, the movement frequency data, the final area data, the reaching time data), and the evaluation data described above. The storage unit 222 stores the evaluation program for causing the computer to execute: a process of displaying an image; a process of detecting the position of the gaze point of the subject observing the display screen; a process of performing the display operation including the first display operation to display the specific object on the display screen and the second display operation to display, on the display screen, the specific object and the comparison objects different from the specific object after performing the first display operation; a process of setting the specific area corresponding to the specific object and the comparison areas corresponding to the comparison objects on the display screen; a process of determining whether the gaze point is present in the specific area and the comparison areas during the display period in which the second display operation is performed, based on the positional data of the gaze point, and output the determination data; a process of calculating the movement progress data indicating the progress of movement of the gaze point during the display period based on the determination data; a process of obtaining the evaluation data of the subject based on the movement progress data; and a process of outputting the evaluation data.

The output control unit 226 outputs data to at least one of the display device 101 and the output device 50.

Figure 4:
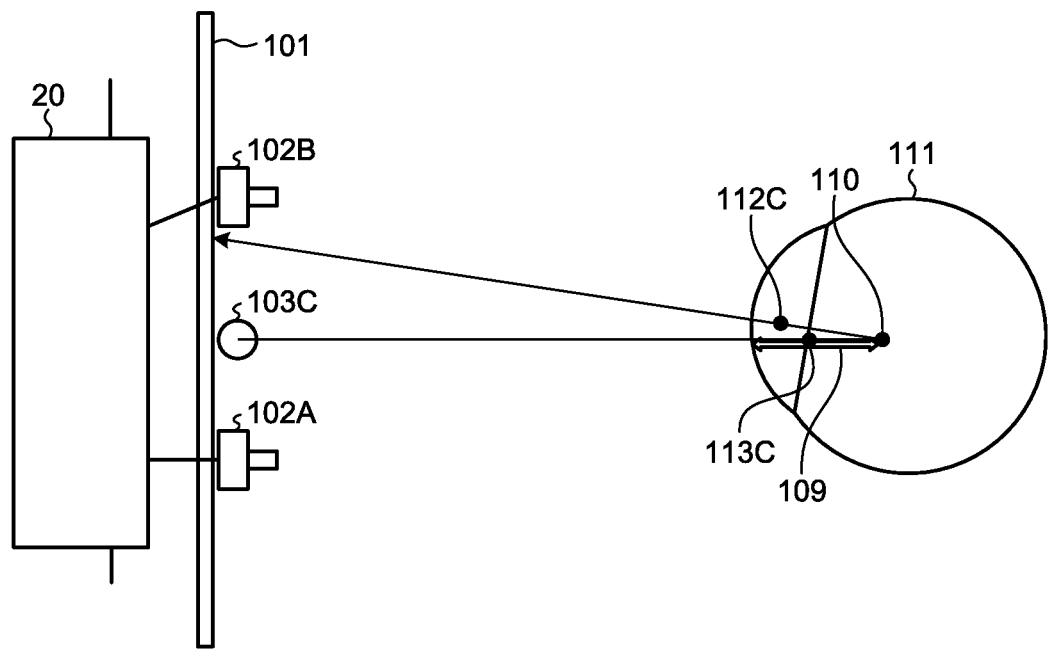
FIG. 4 is a schematic view illustrating a method for calculating the positional data of a corneal curvature center according to the embodiment.
Figure 5:
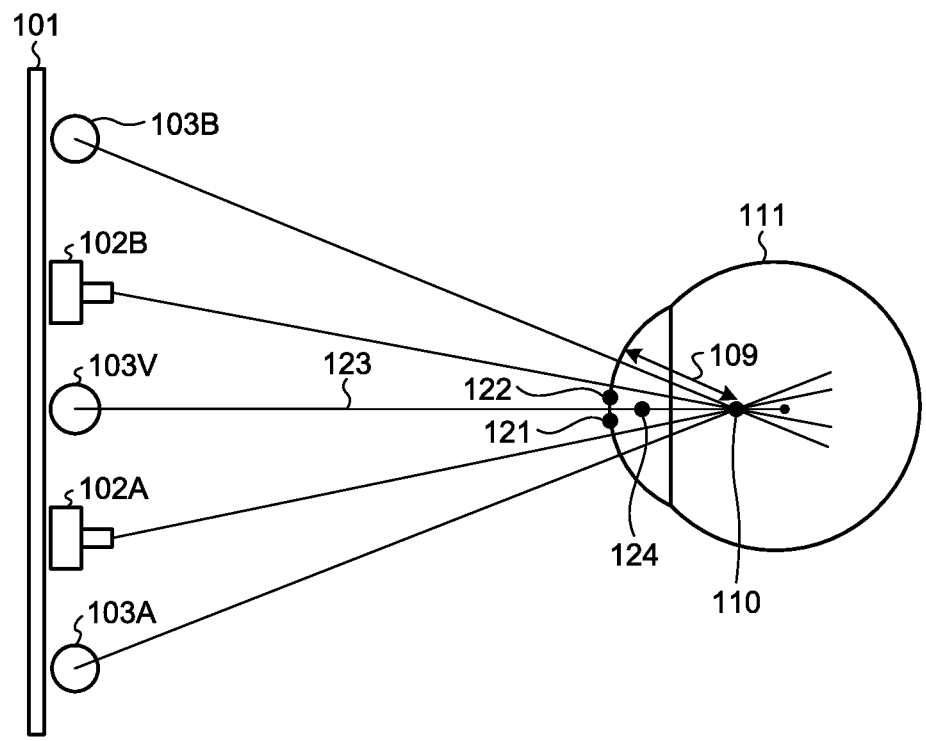
FIG. 5 is a schematic view illustrating a method for calculating the positional data of the corneal curvature center according to the embodiment.

Next, the overview of the process by the curvature center calculating unit 212 according to the embodiment is described. The curvature center calculating unit 212 calculates the positional data of the corneal curvature center of the eyeball 111 based on the image data of the eyeball 111. FIG. 4 and FIG. 5 are schematic views illustrating a method for calculating the positional data of a corneal curvature center 110 according to the embodiment. FIG. 4 illustrates an example in which the eyeball 111 is illuminated by a single light source 103C. FIG. 5 illustrates an example in which the eyeball 111 is illuminated by the first light source 103A and the second light source 103B.

First, the example illustrated in FIG. 4 is described. The light source 103C is disposed between the first camera 102A and the second camera 102B. A pupil center 112C is the center of the pupil 112. A corneal reflection center 113C is the center of the corneal reflection image 113. In FIG. 4, the pupil center 112C indicates the pupil center when the eyeball 111 is illuminated by the single light source 103C. The corneal reflection center 113C indicates the corneal reflection center when the eyeball 111 is illuminated by the single light source 103C. The corneal reflection center 113C exists on a straight line connecting the light source 103C and the corneal curvature center 110. The corneal reflection center 113C is positioned at the midpoint between the corneal surface and the corneal curvature center 110. A corneal curvature radius 109 is a distance between the corneal surface and the corneal curvature center 110. The stereo camera device 102 detects the positional data of the corneal reflection center 113C. The corneal curvature center 110 exists on a straight line connecting the light source 103C and the corneal reflection center 113C. The curvature center calculating unit 212 calculates, as the positional data of the corneal curvature center 110, a positional date of which the distance from the corneal reflection center 113C on the straight line has a predetermined value. The predetermined value is a value previously determined based on, for example, the typical curvature radius value of the cornea and is stored in the storage unit 222.

Next, the example illustrated in FIG. 5 is described. According to the embodiment, the first camera 102A and the first light source 103A are arranged at positions bilaterally symmetrical to the second camera 102B and the second light source 103B with respect to a straight line passing through an intermediate position between the first camera 102A and the second camera 102B. It may be considered that a virtual light source 103V is present at the intermediate position between the first camera 102A and the second camera 102B. A corneal reflection center 121 indicates the corneal reflection center in an image obtained when the second camera 102B captures the eyeball 111. A corneal reflection center 122 indicates the corneal reflection center in an image obtained when the first camera 102A captures the eyeball 111. A corneal reflection center 124 indicates the corneal reflection center corresponding to the virtual light source 103V. The positional data of the corneal reflection center 124 is calculated based on the positional data of the corneal reflection center 121 and the positional data of the corneal reflection center 122 captured by the stereo camera device 102. The stereo camera device 102 detects the positional data of the corneal reflection center 121 and the positional data of the corneal reflection center 122 in the three-dimensional local coordinate system defined in the stereo camera device 102. For the stereo camera device 102, camera calibration is previously executed by using a stereo calibration technique, and a conversion parameter is calculated to convert the three-dimensional local coordinate system of the stereo camera device 102 into a three-dimensional global coordinate system. The storage unit 222 stores the conversion parameter. The curvature center calculating unit 212 uses the conversion parameter to convert the positional data of the corneal reflection center 121 and the positional data of the corneal reflection center 122 captured by the stereo camera device 102 into a positional data in the three-dimensional global coordinate system. The curvature center calculating unit 212 calculates the positional data of the corneal reflection center 124 in the three-dimensional global coordinate system based on the positional data of the corneal reflection center 121 and the positional data of the corneal reflection center 122 defined in the three-dimensional global coordinate system. The corneal curvature center 110 exists on a straight line 123 connecting the virtual light source 103V and the corneal reflection center 124. The curvature center calculating unit 212 calculates, as the positional data of the corneal curvature center 110, a positional data of which the distance from the corneal reflection center 124 on the straight line 123 has a predetermined value. The predetermined value is the value previously determined based on, for example, the typical curvature radius value of the cornea and is stored in the storage unit 222.

As described above, even in a case where there are two light sources, the corneal curvature center 110 is calculated by using the same method as that in a case where there is the single light source.

The corneal curvature radius 109 is the distance between the corneal surface and the corneal curvature center 110. Therefore, the positional data of the corneal surface and the positional data of the corneal curvature center 110 are calculated to calculate the corneal curvature radius 109.

Figure 6:
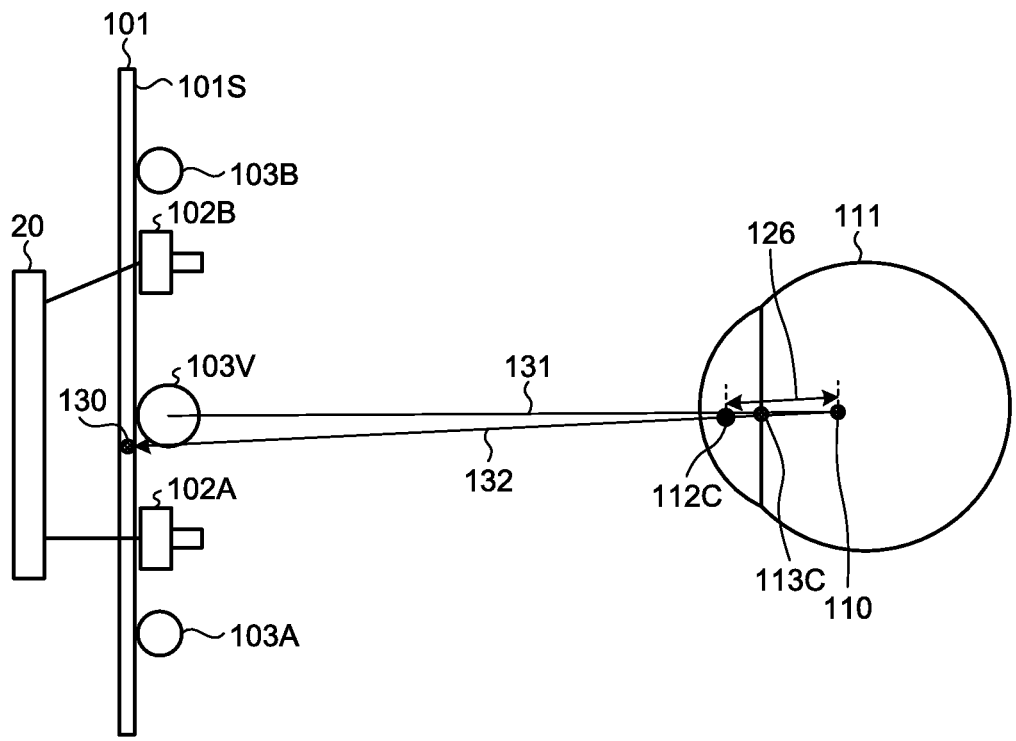
FIG. 6 is a schematic view illustrating an example of a calibration process according to the embodiment.

Next, an example of the method for detecting the line of sight according to the embodiment is described. FIG. 6 is a schematic view illustrating an example of a calibration process according to the embodiment. For the calibration process, a target position 130 is set so that the subject is prompted to gaze at it. The target position 130 is defined in the three-dimensional global coordinate system. In the embodiment, the target position 130 is set at, for example, the central position of the display screen 101S of the display device 101. The target position 130 may be set at an end position of the display screen 101S. The output control unit 226 causes a target image to be displayed at the set target position 130. A straight line 131 is a straight line connecting the virtual light source 103V and the corneal reflection center 113C. A straight line 132 is a straight line connecting the target position 130 and the pupil center 112C. The corneal curvature center 110 is an intersection point between the straight line 131 and the straight line 132. The curvature center calculating unit 212 may calculate the positional data of the corneal curvature center 110 based on the positional data of the virtual light source 103V, the positional data of the target position 130, the positional data of the pupil center 112C, and the positional data of the corneal reflection center 113C.

Figure 7:
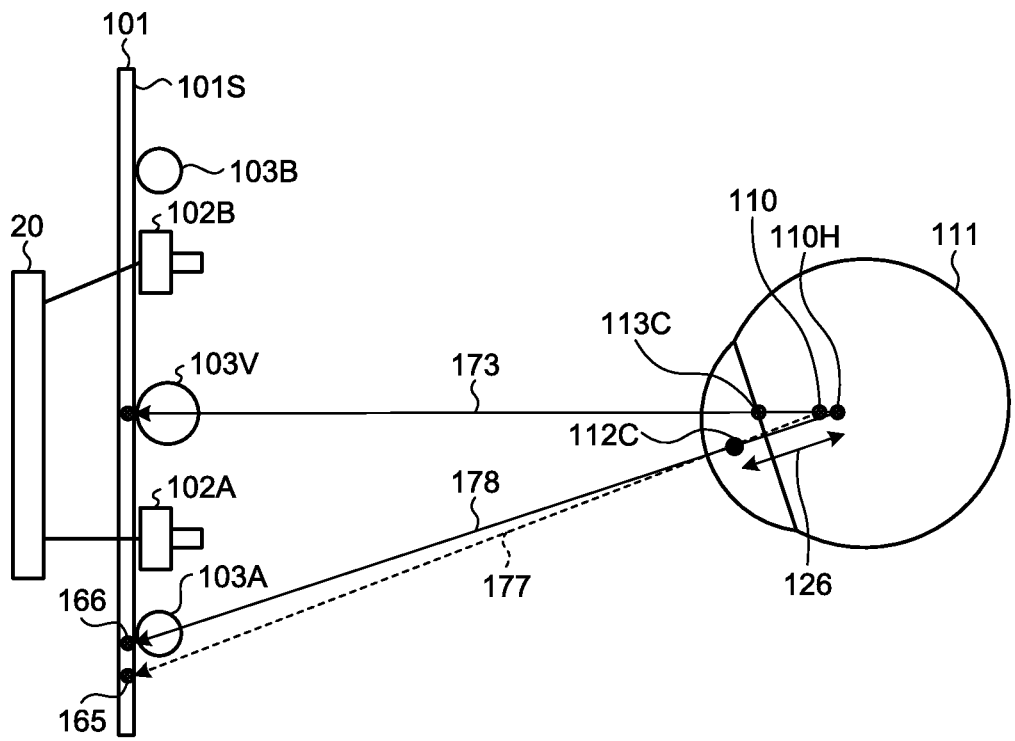
FIG. 7 is a schematic view illustrating an example of a gaze point detection process according to the embodiment.

Next, a gaze point detection process is described. The gaze point detection process is performed after the calibration process. The gaze point detecting unit 214 calculates the eye vector of the subject and the positional data of the gaze point based on the image data of the eyeball 111. FIG. 7 is a schematic view illustrating an example of the gaze point detection process according to the embodiment. In FIG. 7, a gaze point 165 indicates a gaze point obtained from the corneal curvature center calculated by using a general curvature radius value. A gaze point 166 indicates a gaze point obtained from the corneal curvature center calculated using a distance 126 determined during the calibration process. The pupil center 112C indicates a pupil center calculated during the calibration process, and the corneal reflection center 113C indicates a corneal reflection center calculated during the calibration process. A straight line 173 is a straight line connecting the virtual light source 103V and the corneal reflection center 113C. The corneal curvature center 110 is a position of the corneal curvature center calculated from the typical curvature radius value. The distance 126 is a distance between the pupil center 112C and the corneal curvature center 110 calculated during the calibration process. A corneal curvature center 110H indicates a position of a corrected corneal curvature center obtained after correcting the corneal curvature center 110 by using the distance 126. The corneal curvature center 110H is calculated based on the fact that the corneal curvature center 110 exists on the straight line 173 and the distance between the pupil center 112C and the corneal curvature center 110 is the distance 126. Thus, a line of sight 177 calculated in the case of the use of a general curvature radius value is corrected to a line of sight 178. The gaze point on the display screen 101S of the display device 101 is corrected from the gaze point 165 to the gaze point 166.

[Evaluation Method]

Next, an evaluation method according to the embodiment is described. In the evaluation method according to the embodiment, the above-described line-of-sight detection device 100 is used to evaluate cognitive dysfunction and brain dysfunction such as dementia as the visual function of the subject.

Figure 8:
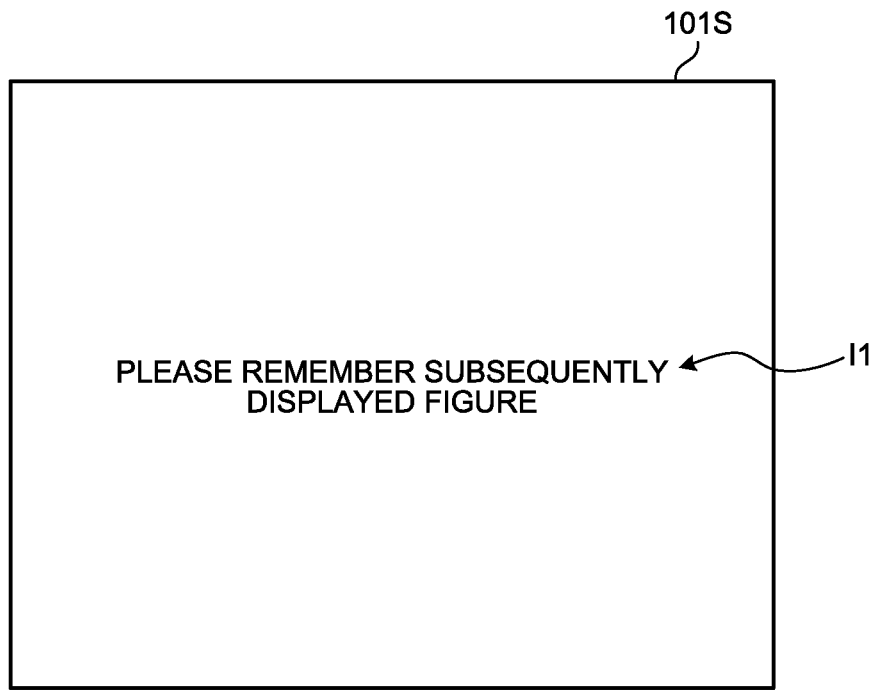
FIG. 8 is a diagram illustrating an example of an instruction displayed on a display screen.

FIG. 8 is a diagram illustrating an example of instruction information I1 displayed on the display screen 101S in the evaluation method according to the embodiment. As illustrated in FIG. 8, the display control unit 202 causes the display screen 101S to display the instruction information I1 for prompting the subject to memorize a subsequently displayed specific object (M1: see FIG. 9).

Figure 9:
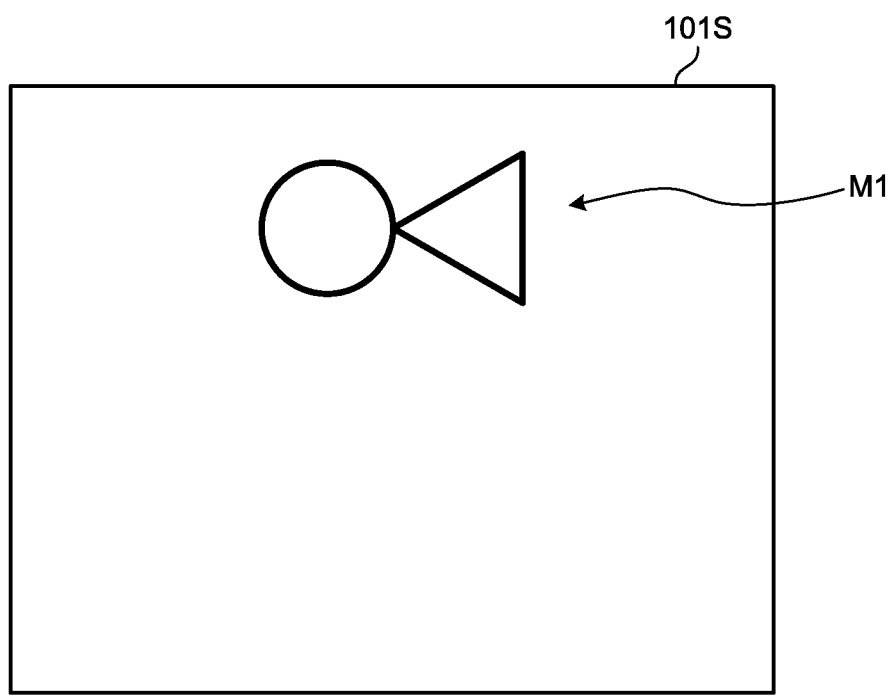
FIG. 9 is a diagram illustrating an example of a specific object displayed on the display screen.

After the display screen 101S displays the instruction information I1, the display control unit 202 causes the display screen 101S to display the specific object during the first display operation. FIG. 9 is a diagram illustrating an example of the specific object M1 displayed on the display screen 101S. As illustrated in FIG. 9, the display control unit 202 causes the specific object M1 having a combinational shape of, for example, but are not limited to, a circle and a triangle during the first display operation. The display control unit 202 causes the display screen 101S to display the specific object M1 for a predetermined period of time (e.g., several seconds) so as to prompt the subject to gaze at the specific object M1 and memorize the specific object M1.

Figure 10:
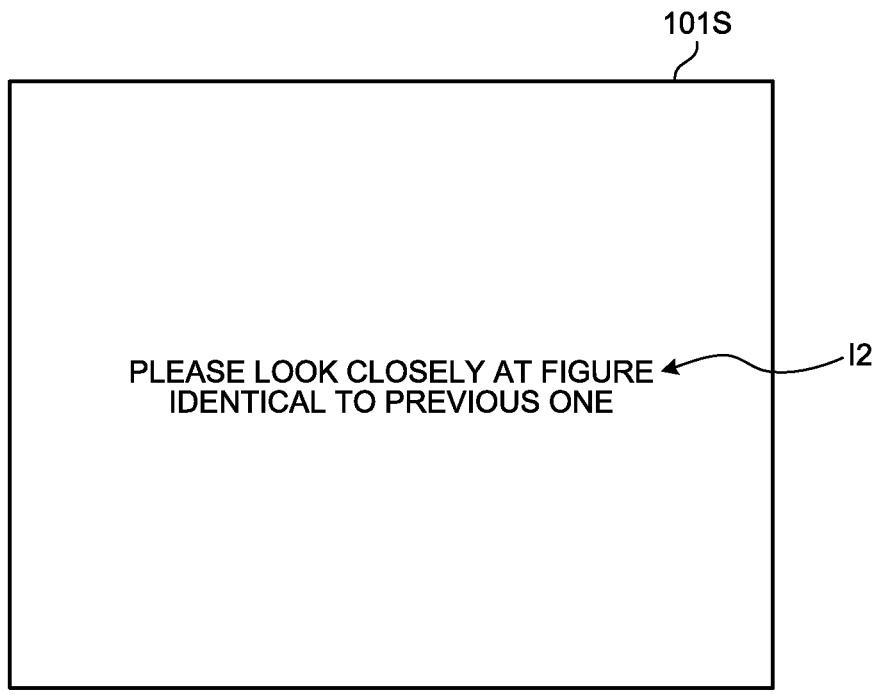
FIG. 10 is a diagram illustrating an example of an instruction displayed on the display screen.

FIG. 10 is a diagram illustrating an example of instruction information I2 displayed on the display screen 101S. As illustrated in FIG. 10, after performing the first display operation for a predetermined period of time, the display control unit 202 causes the display screen 101S to display the instruction information I2 for instructing the subject to gaze at the specific object M1 on the subsequently displayed screen.

Figure 11:
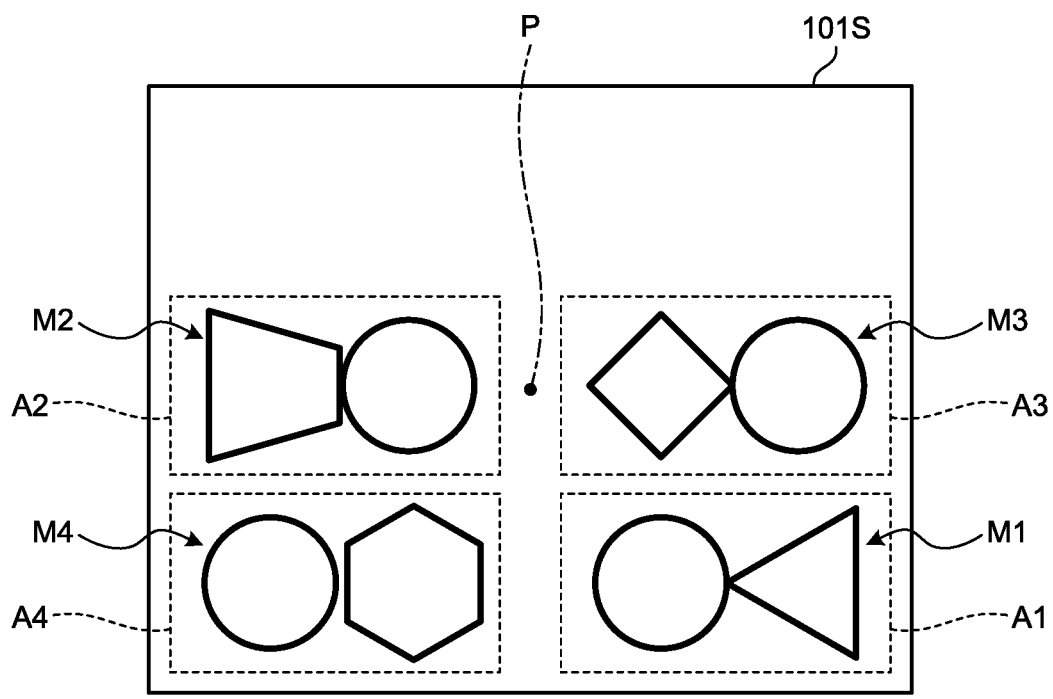
FIG. 11 is a diagram illustrating an example of the case where the display screen displays a specific object and a plurality of comparison objects.

FIG. 11 is a diagram illustrating an example of the case where the display screen 101S displays a plurality of objects. After causing the display screen 101S to display the instruction information I2, the display control unit 202 causes the display screen 101S to display the specific object M1 and a plurality of comparison objects M2 to M4 during the second display operation, as illustrated in FIG. 11.

The comparison objects M2 to M4 may have a shape similar to that of the specific object M1 or may have a shape dissimilar to that of the specific object M1. In the example illustrated in FIG. 11, the comparison object M2 has a combinational shape of a trapezoid and a circle, the comparison object M3 has a combinational shape of a square and a circle, and the comparison object M4 has a combinational shape of a circle and a regular hexagon. The display control unit 202 causes the display screen 101S to display a plurality of objects including the specific object M1 and the comparison objects M2 to M4 so as to prompt the subject to find the specific object M1 and gaze at the found specific object M1.

Although FIG. 11 illustrates an example of a gaze point P that is measured and then displayed as a result on the display screen 101S, the display screen 101S actually does not display the gaze point P. The detection of the positional data of the gaze point is performed, for example, in the cycle (e.g., every 20 [msec]) of frame synchronization signals output from the first camera 102A and the second camera 102B. The first camera 102A and the second camera 102B capture images in synchronization with each other.

During the display period in which the second display operation is performed, the area setting unit 216 sets a specific area A1 corresponding to the specific object M1. The area setting unit 216 sets comparison areas A2 to A4 corresponding to the comparison objects M2 to M4, respectively. The display screen 101S does not display the specific area A1 and the comparison areas A2 to A4.

The area setting unit 216 sets, for example, a rectangular area including the specific object M1 as the specific area A1. Similarly, the area setting unit 216 sets, for example, rectangular areas including the comparison objects M2 to M4 as the comparison areas A2 to A4, respectively. The shapes of the specific area A1 and the comparison areas A2 to A4 are not limited to a rectangle and may be other shapes such as a circle, an ellipse, or a polygon.

It is known that the symptoms of cognitive dysfunction and brain dysfunction affect the memory ability. If the subject does not have cognitive dysfunction nor brain dysfunction, the subject may look at the comparison objects M2 to M4 displayed on the display screen 101S one by one during the second display operation, compares them with the specific object M1 memorized during the first display operation, determines that they are not identical thereto, and finally finds the specific object M1 so as to gaze at it. Conversely, if the subject has cognitive dysfunction or brain dysfunction, the subject sometimes has difficulty in memorizing the specific object M1 or immediately forgets it after memorizing it. Therefore, it is difficult to make a comparison as described above and gaze at the specific object M1.

Thus, it is possible by executing, for example, the following procedure to evaluate the subject. First, in the first display operation, the display screen 101S displays the specific object M1 so as to prompt the subject to memorize it. Then, in the second display operation, the display screen 101S is caused to display the specific object M1 and the comparison objects M2 to M4. In the second display operation, the instruction is given to the subject so as to set the gaze point to the specific object M1. In this case, it is possible to evaluate the subject as to, for example, whether the subject gazes at the comparison objects M2 to M4 one by one, whether the subject is able to finally find the specific object M1 as a correct answer, how long it takes for the subject to find the specific object M1, and whether the subject is able to gaze at the specific object M1.

In the second display operation, when the positional data of the gaze point P of the subject is detected, the determining unit 218 determines whether the gaze point of the subject is present in the specific area A1 and the comparison areas A2 to A4 and outputs the determination data.

Based on the determination data, the calculating unit 220 calculates the movement progress data indicating the progress of movement of the gaze point P during the display period. The calculating unit 220 calculates the presence time data, the movement frequency data, the final area data, and the reaching time data as the movement progress data.

The presence time data indicates the presence time during which the gaze point P is present in the specific area A1. In the embodiment, it may be assumed that the larger the number of times the determining unit 218 determines that the gaze point is present in the specific area A1, the longer the presence time during which the gaze point P is present in the specific area A1. Thus, the presence time data may be the number of times the determining unit 218 determines that the gaze point is present in the specific area A1. That is, the calculating unit 220 may use a count value CNTA of the counter as the presence time data.

The movement frequency data indicates the number of times that the position of the gaze point P moves among the comparison areas A2 to A4 before the gaze point P first reaches the specific area A1. Therefore, the calculating unit 220 may count how many times the gaze point P has moved among the areas: the specific area A1 and the comparison areas A2 to A4, and use, as the movement frequency data, the count result before the gaze point P reaches the specific area A1.

The final area data indicates, among the specific area A1 and the comparison areas A2 to A4, the last area where the gaze point P is finally present in the display time, that is, the last area that is gazed at by the subject as an answer. The calculating unit 220 may update the area where the gaze point P is present every time the gaze point P is detected so as to use the detection result at the end time of the display period as the final area data.

The reaching time data indicates a period of time from when the display period starts to when the gaze point first reaches the specific area A1. Therefore, the calculating unit 220 may measure the elapsed time after the start of the display period by using the timer T1 and, when the gaze point first reaches the specific area A1, set a flag value to 1, and detect the measured value of the timer T1 so as to use the detection result of the timer T1 as the reaching time data.

According to the embodiment, the evaluating unit 224 obtains the evaluation data based on the presence time data, the movement frequency data, the final area data, and the reaching time data.

Here, the data value of the final area data is D1, the data value of the presence time data is D2, the data value of the reaching time data is D3, and the data value of the movement frequency data is D4. Here, the data value D1 of the final area data is 1 when the gaze point P of the subject is finally present in the specific area A1 (that is, a correct answer) and is 0 when it is not present in the specific area A1 (that is, an incorrect answer). The data value D2 of the presence time data is the number of seconds during which the gaze point P is present in the specific area A1. The upper limit value, which is the number of seconds less than the display period, may be provided for the data value D2. The data value D3 of the reaching time data is the reciprocal of the reaching time (for example, 1/(reaching time))/10 (10: a coefficient for setting the reaching-time evaluation value 1 or less when the minimum value of the reaching time is 0.1 seconds). The counter value is directly used as the data value D4 of the movement frequency data. The upper limit value may be provided for the data value D4 as appropriate.

In this case, an evaluation value ANS is, for example, represented as follows:

$$ANS = D1 \cdot K1 + D2 \cdot K2 + D3 \cdot K3 + D4 \cdot K4$$

where K1 to K4 are constants for weighting. The constants K1 to K4 may be set as appropriate.

The evaluation value ANS represented by the above equation is larger when the data value D1 of the final area data is 1, when the data value D2 of the presence time data is larger, when the data value D3 of the reaching time data is larger, and when the value of the data value D4 of the movement frequency data is larger. That is, the evaluation value ANS is larger when the gaze point P is finally present in the specific area A1, the presence time of the gaze point P in the specific area A1 is longer, the reaching time from when the display period starts to when the gaze point P reaches the specific area A1 is shorter, and the movement frequency of the gaze point P moving among the areas is higher.

Conversely, the evaluation value ANS is smaller when the data value D1 of the final area data is 0, when the data value D2 of the presence time data is smaller, when the data value D3 of the reaching time data is smaller, and when the data value D4 of the movement frequency data is smaller. That is, the evaluation value ANS is smaller when finally the gaze point P is not present in the specific area A1, the presence time of the gaze point P in the specific area A1 is shorter, the reaching time from when the display period starts to when the gaze point P reaches the specific area A1 is longer, and when the movement frequency of the gaze point P moving among the areas is lower.

Thus, the evaluating unit 224 may determine whether the evaluation value ANS is greater than a predetermined value to obtain the evaluation data. For example, when the evaluation value ANS is equal to or greater than the predetermined value, it may be evaluated that the subject is unlikely to be a person having cognitive dysfunction and brain dysfunction. Conversely, when the evaluation value ANS is less than the predetermined value, it may be evaluated that the subject is likely to be a person having cognitive dysfunction and brain dysfunction.

The evaluating unit 224 may store the value of the evaluation value ANS in the storage unit 222. For example, the evaluation values ANS for the identical subject may be cumulatively stored and be compared with the previous evaluation value so as to make an evaluation. For example, when the evaluation value ANS is higher than the previous evaluation value, it may be evaluated that the brain function has been improved as compared with the previous evaluation. For example, when the cumulative value of the evaluation value ANS is gradually increased, it may be evaluated that the brain function has been gradually improved.

The evaluating unit 224 may make an evaluation by using, individually or in combination, the presence time data, the movement frequency data, the final area data, and the reaching time data. For example, when the gaze point P accidentally reaches the specific area A1 while the subject views many objects, the data value D4 of the movement frequency data is small. In this case, it is possible to make an evaluation in combination with the data value D2 of the above-described presence time data. For example, when the presence time is long even though the movement frequency is low, it may be evaluated that the specific area A1, which is a correct answer, has been gazed at. When the movement frequency is low and the presence time is short, it may be evaluated that the gaze point P has accidentally passed through the specific area A1.

When the movement frequency is low and the final area is the specific area A1, for example, it may be evaluated that the specific area A1 as a correct answer is reached with a few movements of the gaze point. Conversely, when the movement frequency described above is low and the last area is not the specific area A1, for example, it may be evaluated that the gaze point P has accidentally passed through the specific area A1.

According to the embodiment, when the evaluating unit 224 outputs the evaluation data, the output control unit 226 may cause the output device 50 to output, for example, the text data "the subject seems to be unlikely to have cognitive dysfunction and brain dysfunction" or the text data "the subject seems to be likely to have cognitive dysfunction and brain dysfunction" based on the evaluation data. When the evaluation value ANS for the identical subject is higher than the previous evaluation value ANS, the output control unit 226 may cause the output device 50 to output the text data such as "the brain function has been improved".

Figure 12:
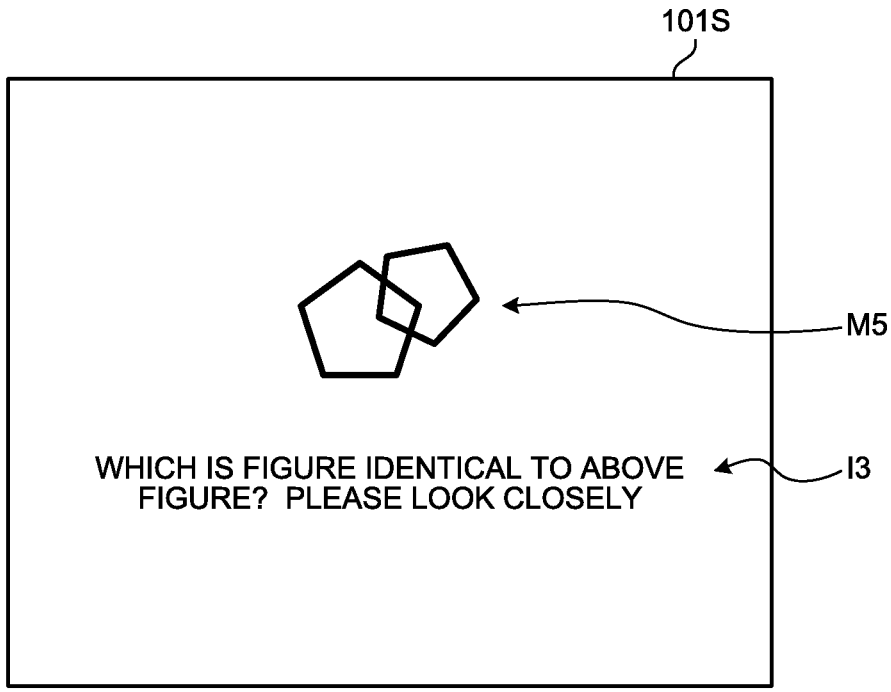
FIG. 12 is a diagram illustrating another example of the case where the display screen displays an instruction and a specific object.
Figure 13:
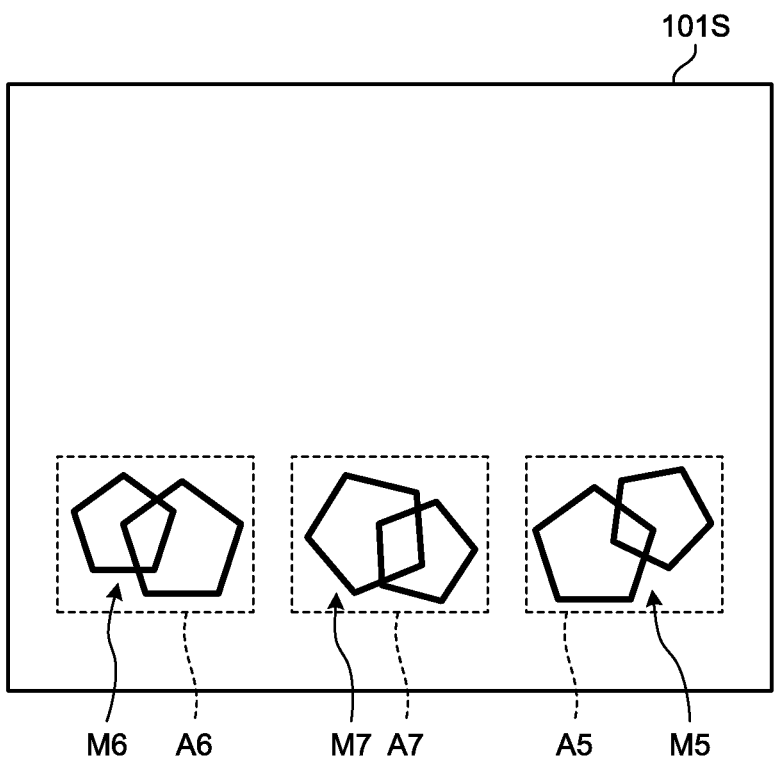
FIG. 13 is a diagram illustrating another example of the case where the display screen displays the specific object and a plurality of comparison objects.

FIG. 12 is a diagram illustrating an example of the case where the display screen 101S simultaneously displays the specific object and instruction information 13. FIG. 13 is a diagram illustrating another example of the case where the display screen 101S displays the specific object and a plurality of comparison objects. As illustrated in FIG. 12, in the first display operation, the display control unit 202 may cause the display screen 101S to display a specific object M5 and also cause the display screen 101S to simultaneously display the instruction information 13 for instructing the subject to gaze at a figure identical to the specific object M5. After the first display operation, the display control unit 202 may cause the specific object M5 and comparison objects M6, M7 to be displayed during the second display operation, as illustrated in FIG. 13. In this case, the display control unit 202 may cause figures formed by using the same shape (e.g., pentagon) such as the specific object M5 and the comparison objects M6, M7 to be displayed. As described above, as the specific object M5 and the comparison objects M6, M7 are displayed as similar figures, it is also possible to evaluate the figure recognition function of the subject. The area setting unit 216 may set a specific area A5 corresponding to the specific object M5 and comparison areas A6, A7 corresponding to the comparison objects M6, M7. As described above, as the specific object M5 and the instruction information 13 are simultaneously displayed on the display screen 101S, it is possible to shorten the examination time.

Figure 14:
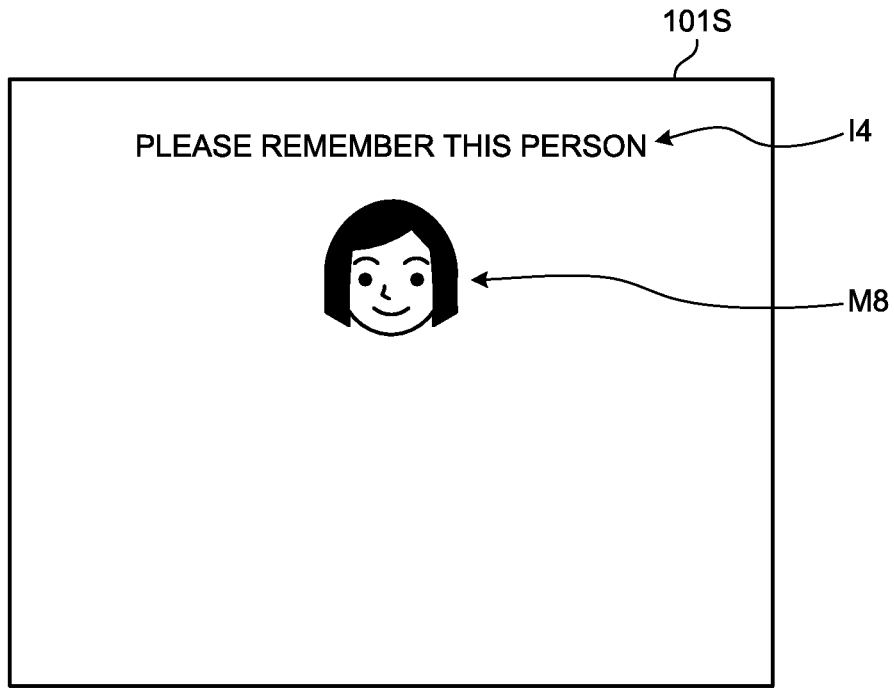
FIG. 14 is a diagram illustrating another example of the case where the display screen displays an instruction and a specific object.
Figure 15:
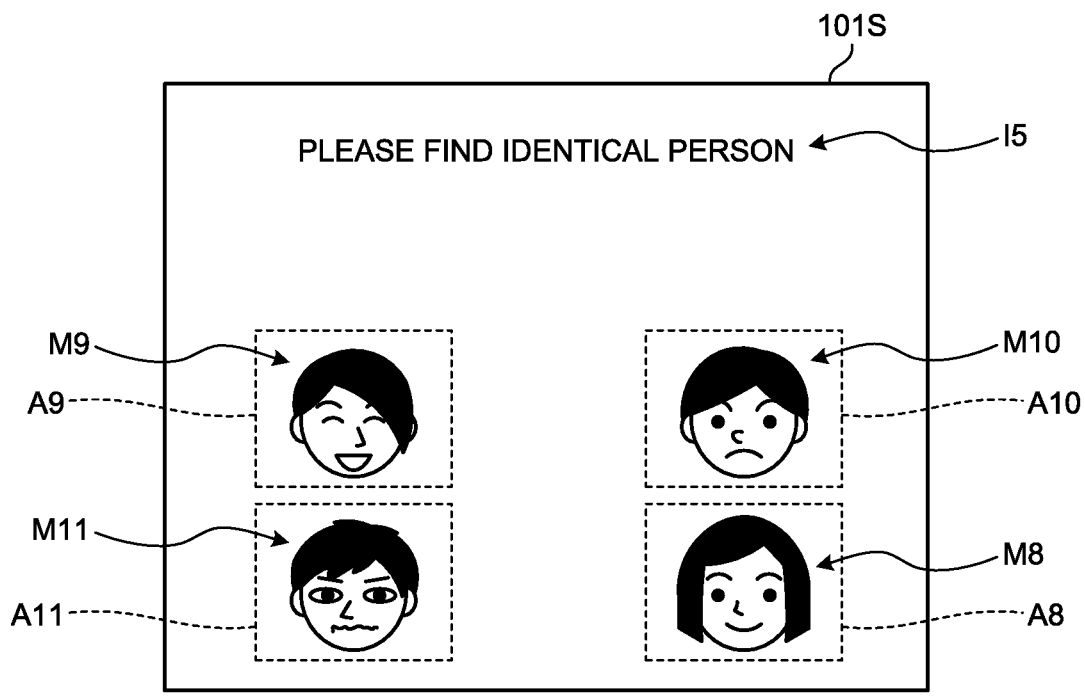
FIG. 15 is a diagram illustrating another example of the case where the display screen displays the specific object and a plurality of comparison objects.

FIG. 14 is a diagram illustrating another example of the case where the display screen 101S displays a specific object and instruction information 14. FIG. 15 is a diagram illustrating another example of the case where the display screen 101S displays the specific object and a plurality of comparison objects. As illustrated in FIG. 14, in the first display operation, the display control unit 202 may cause the face of a person to be displayed as a specific object M8. In this case, the display control unit 202 may cause the specific object M8 and the instruction information 14 to be displayed simultaneously. As illustrated in FIG. 14, the instruction information may have contents to instruct the subject so as to memorize the person that is the specific object M8.

In the second display operation after the first display operation, the display control unit 202 may cause the specific object M8 and comparison objects M9 to M11, which are the faces of persons different from the specific object M8, to be displayed as illustrated in FIG. 15. The area setting unit 216 may set a specific area A8 corresponding to the specific object M8 and set comparison areas A9 to A11 corresponding to the comparison objects M9 to M11. As illustrated in FIG. 15, in the second display operation, the display control unit 202 may cause the specific object M8, the comparison objects M9 to M11, and the instruction information 15 to be simultaneously displayed. As described above, the display control unit 202 may cause instruction information to be displayed for each of the first display operation and the second display operation. Thus, it is possible to further shorten the examination time.

Figure 16:
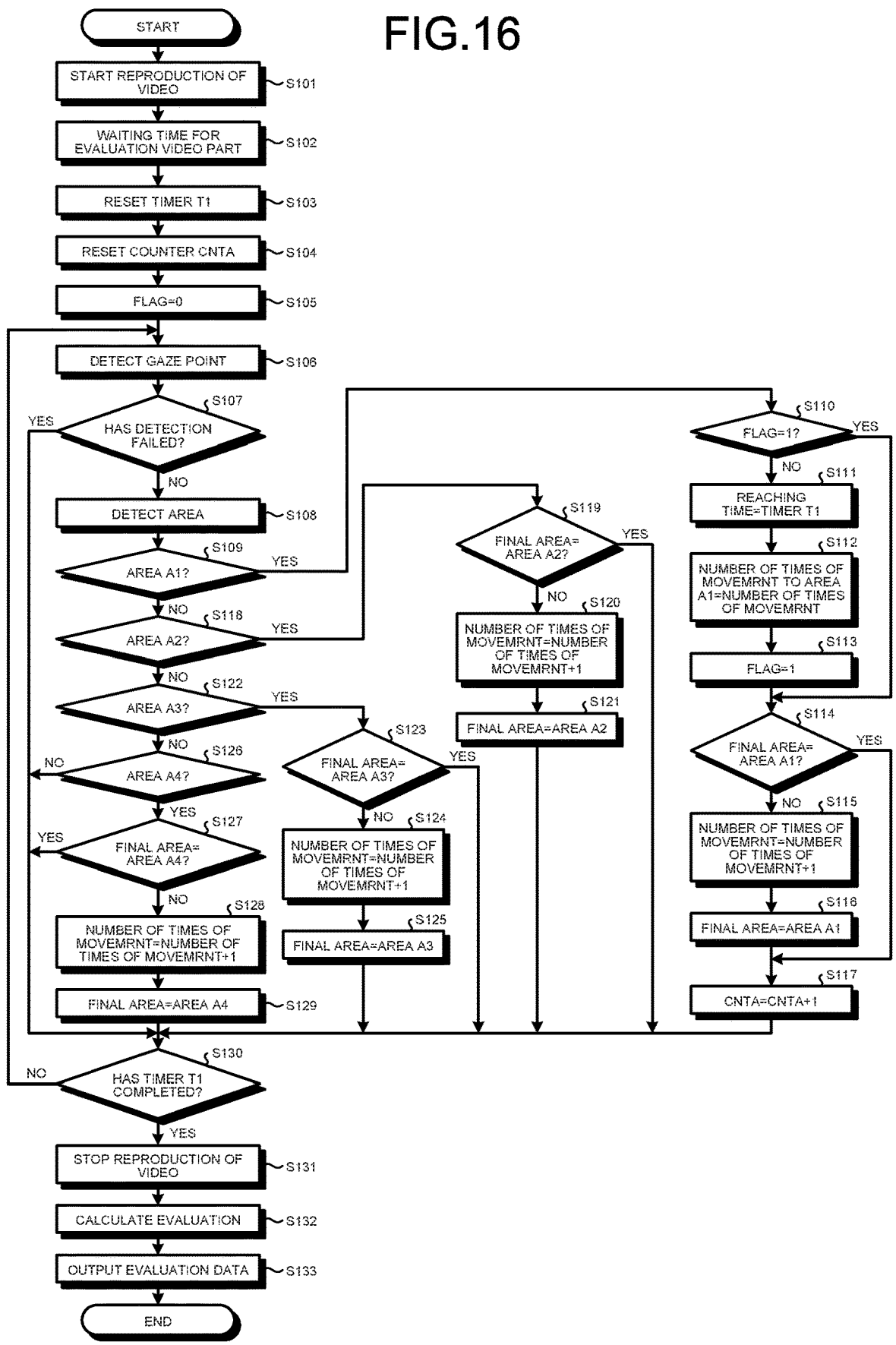
FIG. 16 is a flowchart illustrating an example of an evaluation method according to the embodiment.

Next, an example of the evaluation method according to the embodiment is described with reference to FIG. 16. FIG. 16 is a flowchart illustrating an example of the evaluation method according to the embodiment. According to the embodiment, the display control unit 202 starts the reproduction of a video (Step S101). On the display screen 101S, after the waiting time for the evaluation video part has elapsed (Step S102), the timer T1 is reset (Step S103), the count value CNTA of the counter is reset (Step S104), and the flag value is set to 0 (Step S105).

While the subject looks at the video displayed on the display device 101, the gaze point detecting unit 214 detects the positional data of the gaze point of the subject on the display screen 101S of the display device 101 for each predetermined sampling period (e.g., 20 [msec]) (Step S106). When the positional data is detected (No at Step S107), the determining unit 218 determines the area where the gaze point P is present based on the positional data (Step S108).

When it is determined that the gaze point P is present in the specific area A1 (Yes at Step S109), the calculating unit 220 determines whether the flag value is 1, that is, whether the gaze point P has first reached the specific area A1 (1: has reached, 0: has not reached) (Step S110). When the flag value is 1 (Yes at Step S110), the calculating unit 220 skips the following Step S111 to Step S113 and performs the operation at Step S114 described later.

When the flag value is not 1, that is, when the gaze point P has first reached the specific area A1 (No at Step S110), the calculating unit 220 extracts the measurement result of the timer T1 as the reaching time data (Step S111). The calculating unit 220 stores, in the storage unit 222, the movement frequency data indicating how many times the gaze point P has moved among the areas before reaching the specific area A1 (Step S112). Then, the calculating unit 220 changes the flag value to 1 (Step S113).

Subsequently, the calculating unit 220 determines whether the area where the gaze point P is present during the most recent detection, that is, the final area, is the specific area A1 (Step S114). When it is determined that the final area is the specific area A1 (Yes at Step S114), the calculating unit 220 skips the following Step S115 and Step S116 and performs the operation at Step S117 described later. When it is determined that the final area is not the specific area A1 (No at Step S114), the calculating unit 220 increments by one the number of times of movement indicating how many times the gaze point P has moved among the areas (Step S115) and changes the final area to the specific area A1 (Step S116). The calculating unit 220 increments by one the count value CNTA indicating the presence time data of the specific area A1 (Step S117). Then, the calculating unit 220 performs the process starting from Step S130 described later.

When it is determined that the gaze point P is not present in the specific area A1 (No at Step S109), the calculating unit 220 determines whether the gaze point P is present in the comparison area A2 (Step S118). When it is determined that the gaze point P is present in the comparison area A2 (Yes at Step S118), the calculating unit 220 determines whether the area where the gaze point P is present during the most recent detection, that is, the final area, is the comparison area A2 (Step S119). When it is determined that the final area is the comparison area A2 (Yes at Step S119), the calculating unit 220 skips the subsequent Step S120 and Step 121 and performs the operation at Step S130 described later. When it is determined that the final area is not the comparison area A2 (No at Step S119), the calculating unit 220 increments by one the number of times of movement indicating how many times the gaze point P has moved among the areas (Step S120) and changes the final area to the comparison area A2 (Step S121). Then, the calculating unit 220 performs the process starting from Step S130 described later.

When it is determined that the gaze point P is not present in the comparison area A2 (No at Step S118), the calculating unit 220 determines whether the gaze point P is present in the comparison area A3 (Step S122). When it is determined that the gaze point P is present in the comparison area A3 (Yes at Step S122), the calculating unit 220 determines whether the area where the gaze point P is present during the most recent detection, that is, the final area, is the comparison area A3 (Step S123). When it is determined that the final area is the comparison area A3 (Yes at Step S123), the calculating unit 220 skips the subsequent Step S124 and S125 and performs the operation at Step S130 described below. When it is determined that the final area is not the comparison area A3 (No at Step S123), the calculating unit 220 increments by one the number of times of movement indicating how many times the gaze point P has moved among the areas (Step S124) and changes the final area to the comparison area A3 (Step S125). Then, the calculating unit 220 performs the operation starting from Step S130 described later.

When it is determined that the gaze point P is not present in the comparison area A3 (No at Step S122), the calculating unit 220 determines whether the gaze point P is present in the comparison area A4 (Step S126). When it is determined that the gaze point P is present in the comparison area A4 (Yes at Step S126), the calculating unit 220 determines whether the area where the gaze point P is present during the most recent detection, that is, the final area, is the comparison area A4 (Step S127). When it is determined that the final area is the comparison area A4 (Yes at Step S127), the calculating unit 220 skips the subsequent Step S128 and Step S129 and performs the operation at Step S130 described later. When it is determined that the final area is not the comparison area A4 (No at Step S127), the calculating unit 220 increments by one the number of times of movement indicating how many times the gaze point P has moved among the areas (Step S128) and changes the final area to the comparison area A3 (Step S129). Then, the calculating unit 220 performs the process starting from Step S130 described later.

Subsequently, the calculating unit 220 determines whether the video reproduction completion time has reached, based on the detection result of the detection timer T1 (Step S130). When the calculating unit 220 determines that the video reproduction completion time has not reached (No at Step S130), the above-described process starting from Step S106 is repeatedly performed.

When the calculating unit 220 determines that the video reproduction completion time has reached (Yes at Step S130), the display control unit 202 stops the reproduction of the video (Step S131). After the reproduction of the video is stopped, the evaluating unit 224 calculates the evaluation value ANS based on the presence time data, the movement frequency data, the final area data, and the reaching time data obtained from the above-described processing result (Step S132) and obtains the evaluation data based on the evaluation value ANS. Then, the output control unit 226 outputs the evaluation data obtained by the evaluating unit 224 (Step S133).

As described above, the evaluation apparatus according to the embodiment includes: the gaze point detecting unit 214 that detects the position of the gaze point of the subject observing the image displayed on the display screen 101S; the display control unit 202 that performs the display operation including the first display operation to display the specific object M1 on the display screen 101S and the second display operation to display, on the display screen 101S, the specific object M1 and the comparison objects M2 to M4 different from the specific object M1 after performing the first display operation; the area setting unit 216 that sets the specific area A1 corresponding to the specific object M1 and the comparison areas A2 to A4 corresponding to the comparison objects M2 to M4 on the display screen 101S; the determining unit 218 that, based on the positional data of the gaze point P, determines whether the gaze point P is present in the specific area A1 and the comparison areas A2 to A4 during the display period in which the second display operation is performed; the calculating unit 220 that calculates the movement progress data indicating the progress of movement of the gaze point P in the display period based on the determination result; and the evaluating unit 224 that obtains the evaluation data of the subject based on the movement progress data.

The evaluation method according to the embodiment includes: detecting the position of the gaze point of the subject observing the image displayed on the display screen 101S; performing the display operation including the first display operation to display the specific object M1 on the display screen 101S and the second display operation to display, on the display screen 101S, the specific object M1 and the comparison objects M2 to M4 different from the specific object M1 after performing the first display operation; setting the specific area A1 corresponding to the specific object M1 and the comparison areas A2 to A4 corresponding to the comparison objects M2 to M4 on the display screen 101S; determining, based on the positional data of the gaze point P, whether the gaze point P is present in the specific area A1 and the comparison areas A2 to A4 during the display period in which the second display operation is performed; calculating the movement progress data indicating the progress of movement of the gaze point P in the display period based on the determination result; obtaining the evaluation data of the subject based on the movement progress data; and outputting the evaluation data.

The evaluation program according to the embodiment causes the computer to execute: the process of detecting the position of the gaze point of the subject observing the image displayed on the display screen 101S; the process of performing the display operation including the first display operation to display the specific object M1 on the display screen 101S and the second display operation to display, on the display screen 101S, the specific object M1 and the comparison objects M2 to M4 different from the specific object M1 after performing the first display operation; the process of setting the specific area A1 corresponding to the specific object M1 and the comparison areas A2 to A4 corresponding to the comparison objects M2 to M4 on the display screen 101S; the process of determining, based on the positional data of the gaze point P, whether the gaze point P is present in the specific area A1 and the comparison areas A2 to A4 during the display period in which the second display operation is performed; the process of calculating the movement progress data indicating the progress of movement of the gaze point P in the display period based on the determination result; and the process of obtaining the evaluation data of the subject based on the movement progress data.

According to the embodiment, the evaluation data of the subject may be obtained based on the progress of movement of the gaze point during the display period; therefore, the accidentalness may be reduced, and the memory ability of the subject may be evaluated with high accuracy. Thus, the evaluation apparatus 100 may evaluate the subject with high accuracy.

In the evaluation apparatus 100 according to the embodiment, the gaze point data includes at least one data item among the reaching time data indicating the time from when the display period starts to when the gaze point P first reaches the specific area A1, the movement frequency data indicating the number of times that the position of the gaze point P moves among the comparison areas A2 to A4 before the gaze point P first reaches the specific area A1, the presence time data indicating the presence time during which the gaze point P is present in the specific area A1 or the comparison areas A2 to A4 during the display period, and the final area data indicating the final area in which the gaze point P is finally present during the display period among the specific area A1 and the comparison areas A2 to A4. The evaluating unit 224 obtains the evaluation data of the subject based on at least one data item included in the gaze point data. This makes it possible to efficiently obtain evaluation data with high accuracy.

In the evaluation apparatus 100 according to the embodiment, the evaluating unit 224 applies a weight to at least one data item included in the gaze point data to obtain the evaluation data. Thus, the order of priority is given to each data item to obtain the evaluation data with higher accuracy.

The technical scope of the present disclosure is not limited to the above-described embodiment and may be modified as appropriate without departing from the spirit of the present disclosure. In the example described according to the above embodiment, the evaluation apparatus 100 is used as the evaluation apparatus that evaluates the possibility of the person having cognitive dysfunction and brain dysfunction; however, this is not a limitation. For example, the evaluation apparatus 100 may be used as an evaluation apparatus that evaluates the memory ability of a subject who does not have cognitive dysfunction or brain dysfunction.

In the example described according to the above embodiment, the area setting unit 216 sets the specific area A1 and the comparison areas A2 to A4 during the second display operation; however, this is not a limitation. For example, the area setting unit 216 may set the corresponding area that corresponds to the specific object M1 displayed on the display screen 101S during the first display operation. In this case, the determining unit 218 may determine whether the gaze point P of the subject is present in the corresponding area. The calculating unit 220 may determine whether the subject is able to memorize the specific object M1 displayed on the display screen 101S during the first display operation based on the determination result of the determining unit 218.

In the example described according to the above embodiment, the display form of the specific object has a constant state during the first display operation; however, this is not a limitation. For example, the display control unit 202 may change the display form of the specific object during the first display operation.

Figure 17:
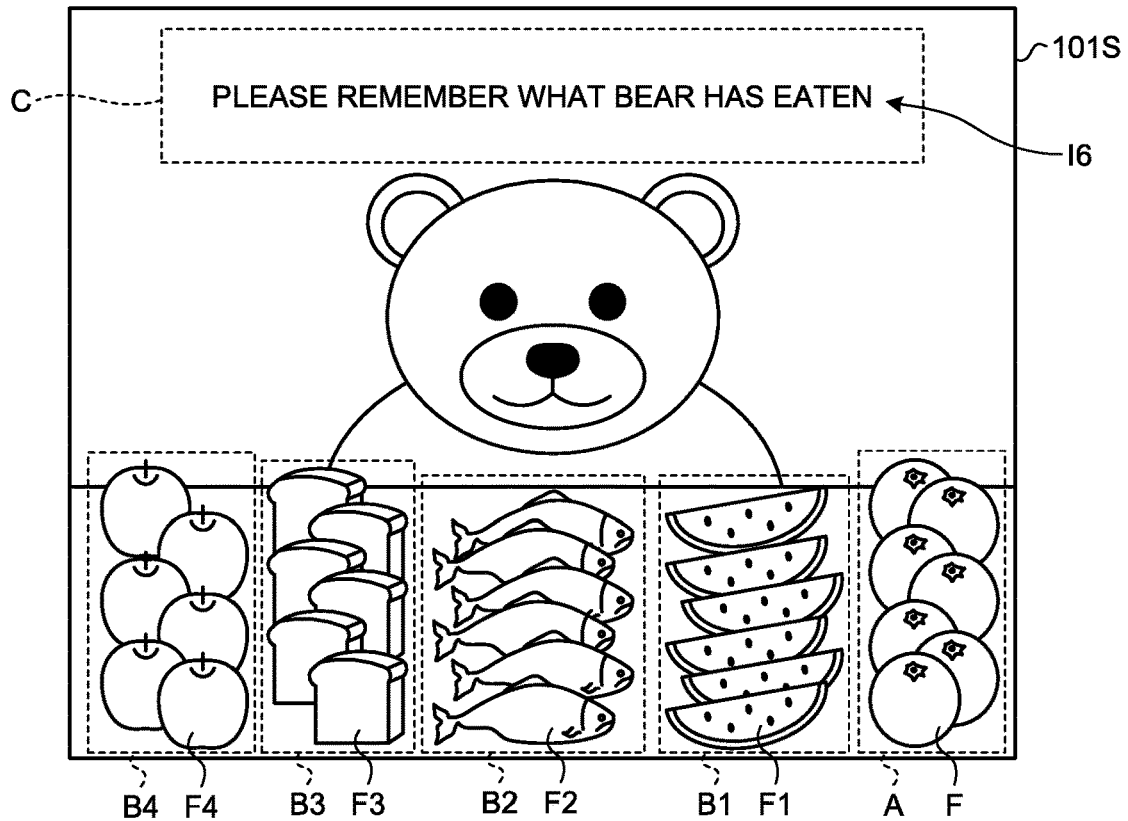
FIG. 17 is a diagram illustrating an example of a series of evaluation images displayed on the display screen.

FIG. 17 to FIG. 23 are diagrams illustrating an example of a series of evaluation images displayed on the display screen 101S. As illustrated in FIG. 17, the display control unit 202 first causes the display screen 101S to display the image in which five types of food are arranged in front of a bear. The five types of food correspond to objects F, F1 to F4. Here, for example, the object F is an orange, the object F1 is a watermelon, the object F2 is fish, the object F3 is bread, and the object F4 is an apple. The display control unit 202 causes instruction information 16 to be displayed so as to prompt the user to memorize the type of food eaten by the bear among the five types of food in the subsequently displayed image (see FIG. 18 to FIG. 20). In the case described below, for example, the bear eats an orange out of the five types of food. In this case, among the objects F, F1 to F4, the object F representing an orange is the specific object. The objects F1 to F4 representing food other than the orange are the comparison objects. Hereinafter, the object F is sometimes referred to as the specific object F, and the objects F1 to F4 are sometimes referred to as the comparison objects F1 to F4.

As illustrated in FIG. 17, the area setting unit 216 sets a specific area A corresponding to the specific object F and sets comparison areas B1 to B4 corresponding to the comparison objects F1 to F4. The area setting unit 216 sets an instruction area C corresponding to the instruction information 16. The area setting unit 216 sets a rectangular area including the specific object F as the specific area A, for example. Similarly, the area setting unit 216 sets rectangular areas including the comparison objects F1 to F4 as the comparison areas B1 to B4, for example. The area setting unit 216 sets a rectangular area including the instruction information 16 as the instruction area C. The shapes of the specific area A, the comparison areas B1 to B4, and the instruction area C are not limited to a rectangle and may be other shapes such as a circle, an ellipse, or a polygon. In this case, the area setting unit 216 sets the specific area A, the comparison areas B1 to B4, and the instruction area C so as not to be overlapped with each other.

Figure 18:
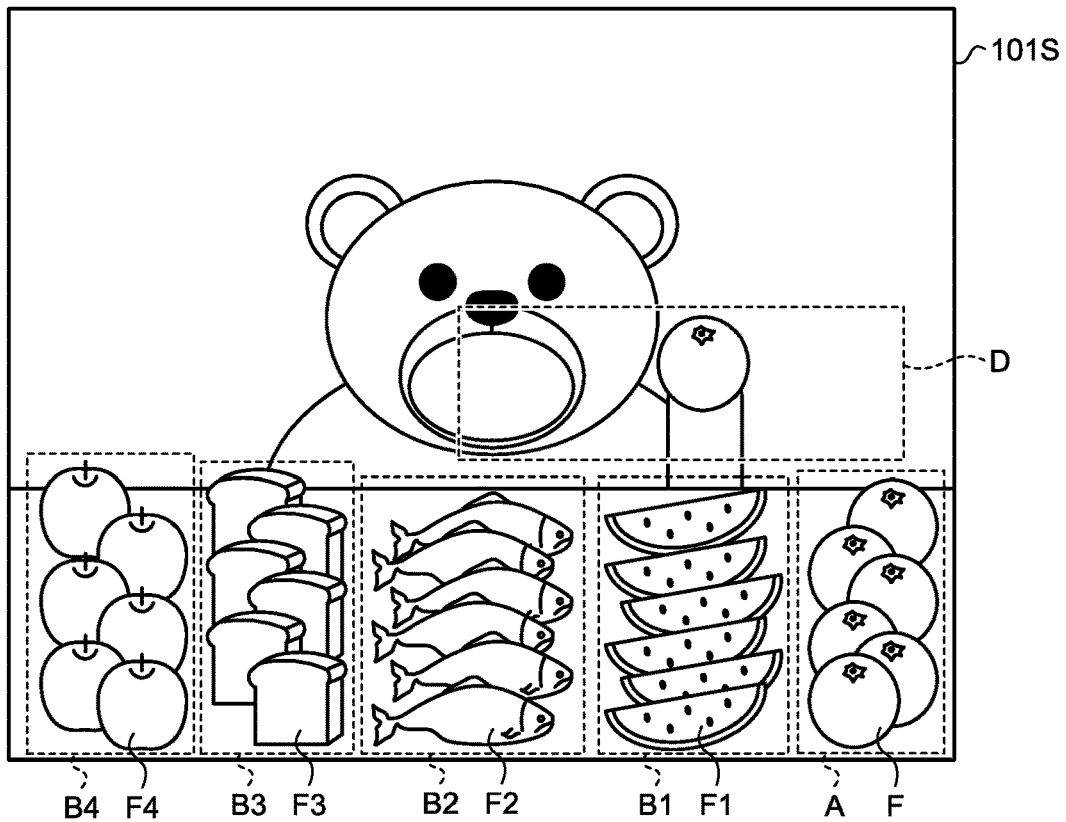
FIG. 18 is a diagram illustrating an example of a series of evaluation images displayed on the display screen.
Figure 19:
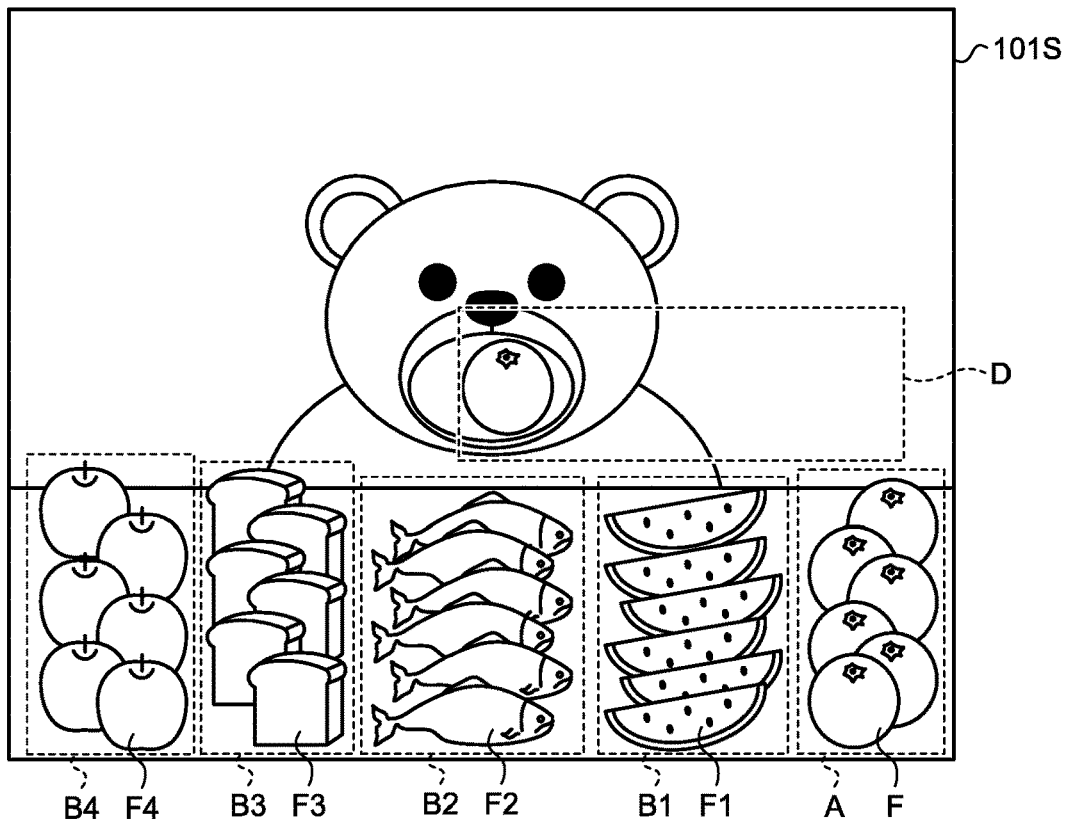
FIG. 19 is a diagram illustrating an example of a series of evaluation images displayed on the display screen.
Figure 20:
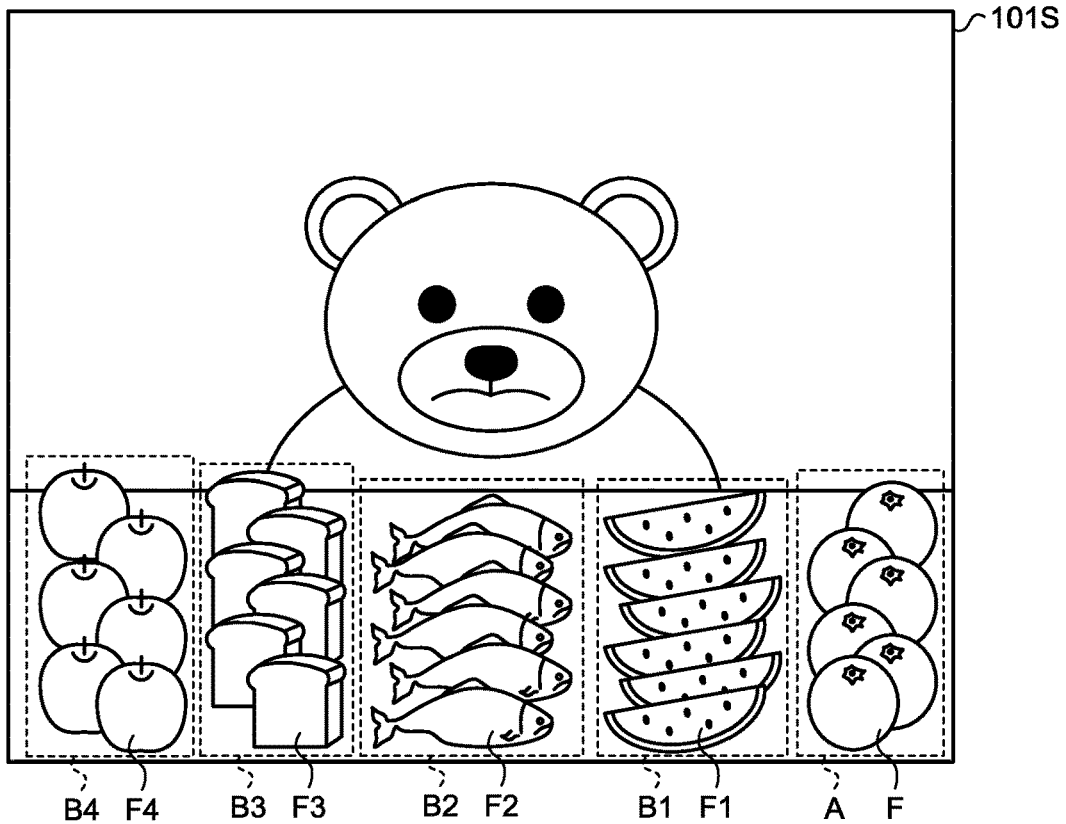
FIG. 20 is a diagram illustrating an example of a series of evaluation images displayed on the display screen.

Subsequently, in the first display operation, the display control unit 202 causes the display screen 101S to display a moving image in which the bear eats one type of food out of the five types of food. FIG. 18 to FIG. 20 are diagrams each illustrating a scene of the moving image. In the case described below, for example, the bear eats an orange. In this case, among the objects F, F1 to F4, the object F representing an orange is the specific object. The objects F1 to F4 representing food other than an orange are the comparison objects. Hereinafter, the object F is sometimes referred to as the specific object F, and the objects F1 to F4 are sometimes referred to as the comparison objects F1 to F4.

FIG. 18 illustrates a scene in which the bear takes an orange with hand and opens its mouth. FIG. 19 illustrates a scene in which the bear puts the orange in its mouth and closes the mouth. FIG. 20 illustrates a scene in which the orange in the bear's mouth is not visible and the bear is eating the orange. In this manner, the display control unit 202 changes the display form of the specific object F. The display screen 101S displays the series of actions of the bear illustrated in FIG. 18 to FIG. 20 so that the subject is prompted to memorize the fact that the bear has eaten the orange out of the five types of food.

As illustrated in FIG. 18 to FIG. 20, the area setting unit 216 sets the specific area A corresponding to the specific object F and sets the comparison areas B1 to B4 corresponding to the comparison objects F1 to F4 continuously from the state illustrated in FIG. 17. The area setting unit 216 cancels the setting of the instruction area C. The area setting unit 216 sets, as a movement area D, a rectangular area including the trajectory of movement of the orange while the bear takes the orange with hand and puts it into its mouth. Even in this case, the shapes of the specific area A, the comparison areas B1 to B4, and the movement area D are not limited to a rectangular shape and may be other shapes such as a circle, an ellipse, or a polygon. In this case, the area setting unit 216 sets the specific area A, the comparison areas B1 to B4, and the movement area D so as not to be overlapped with each other. When the scene in FIG. 20 is displayed after the scene in FIG. 19 is terminated, the area setting unit 216 cancels the setting of the movement area D. That is, the setting of the movement area D is canceled at a predetermined time when the orange in the bear's mouth becomes invisible after the mouth is closed.

Figure 21:
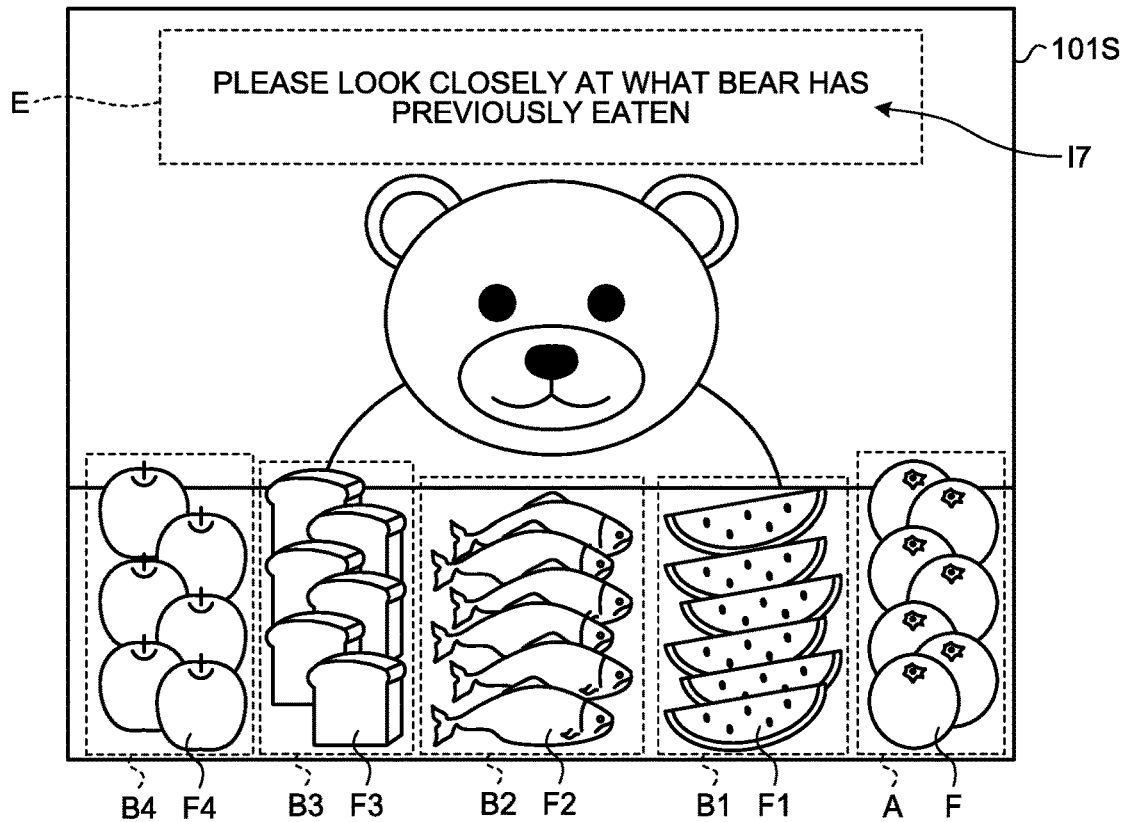
FIG. 21 is a diagram illustrating an example of a series of evaluation images displayed on the display screen.

In the second display operation after the first display operation, the display control unit 202 displays instruction information 17 for causing the subject to gaze at the type of food eaten by the bear among the five type of food while the five types of food are arranged in front of the bear as illustrated in FIG. 21. The area setting unit 216 sets the specific area A corresponding to the specific object F and sets the comparison areas B1 to B4 corresponding to the comparison objects F1 to F4 continuously from the state illustrated in FIG. 20. The area setting unit 216 sets an instruction area E corresponding to the instruction information 17. The shapes of the specific area A, the comparison areas B1 to B4, and the instruction area E are not limited to a rectangular shape and may be other shapes such as a circle, an ellipse, or a polygon. In this case, the area setting unit 216 sets the specific area A, the comparison areas B1 to B4, and the instruction area E so as not to be overlapped with each other.

Figure 22:
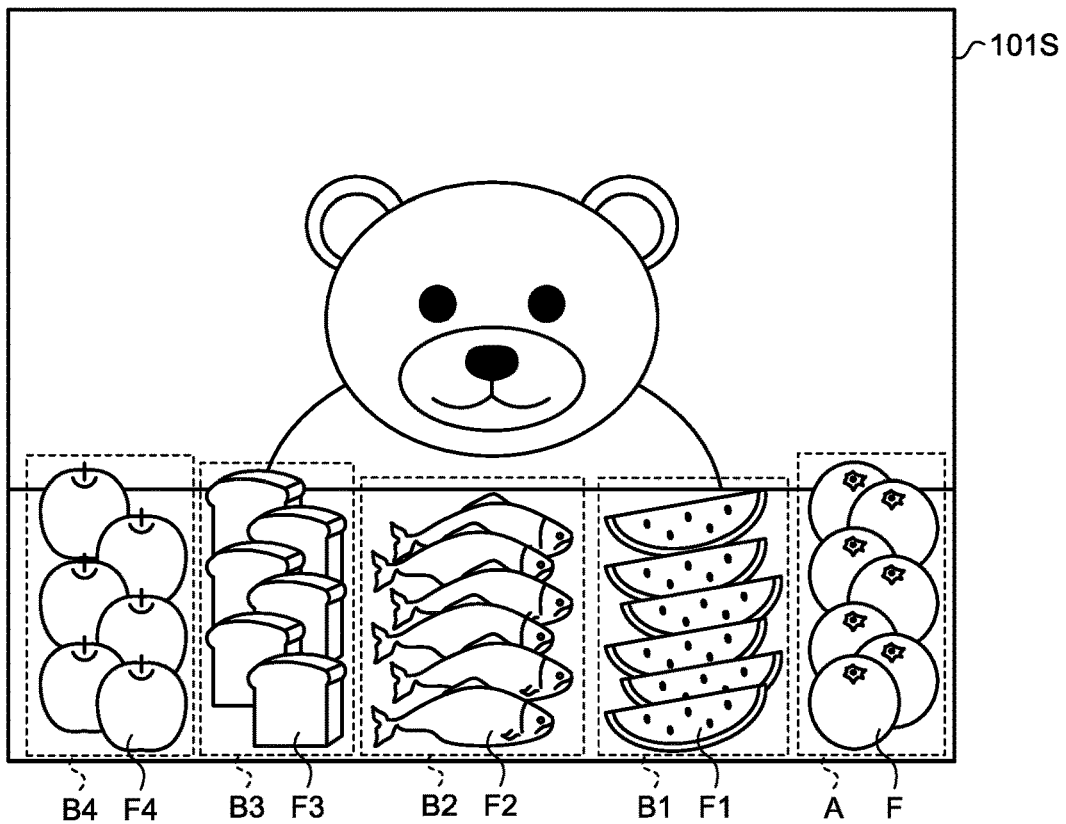
FIG. 22 is a diagram illustrating an example of a series of evaluation images displayed on the display screen.

After the instruction information 17 is displayed for a predetermined period of time, the display control unit 202 deletes the display of the instruction information 17, as illustrated in FIG. 22. The area setting unit 216 cancels the setting of the instruction area E in synchronization with the deletion timing of the display of the instruction information 17. The display control unit 202 and the area setting unit 216 maintain this state for a predetermined period of time. Specifically, the display control unit 202 causes the display screen 101S to display the specific object F and the comparison objects F1 to F4 for a predetermined period of time. The area setting unit 216 sets the specific area A corresponding to the specific object F for a predetermined period of time and sets the comparison areas B1 to B4 corresponding to the comparison objects F1 to F4 for the predetermined period of time. In this predetermined period of time, the subject is prompted to gaze at the specific object F and the comparison objects F1 to F4.

Figure 23:
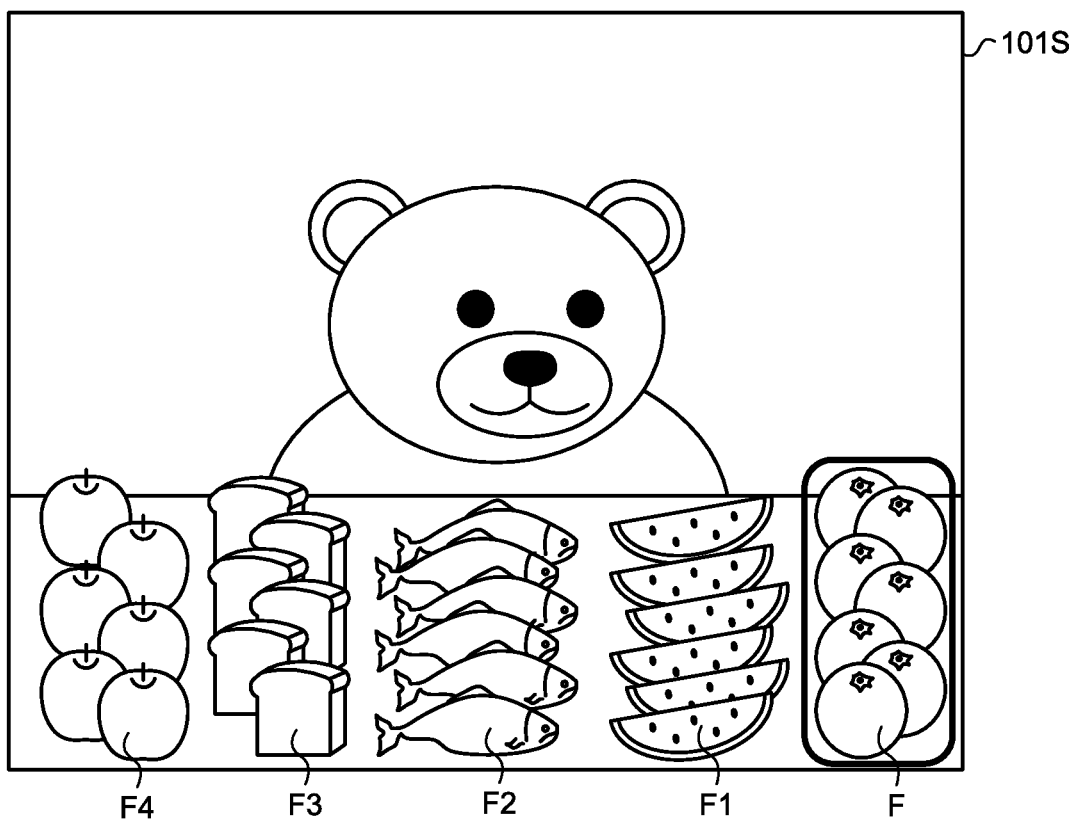
FIG. 23 is a diagram illustrating an example of a series of evaluation images displayed on the display screen.

After the predetermined period of time has elapsed, the display control unit 202 may cause an image indicating the correct answer to the instruction information 17 to be displayed as illustrated in FIG. 23. FIG. 23 illustrates an example of an image in which the area where oranges are placed is surrounded by a frame and the bear is looking at the oranges. Displaying the image in FIG. 23 makes it possible to cause the subject to clearly know the correct answer. When the image indicating the correct answer is displayed, the area setting unit 216 may cancel the specific area A, the comparison areas B1 to B4, and the instruction area E.

Figure 24:
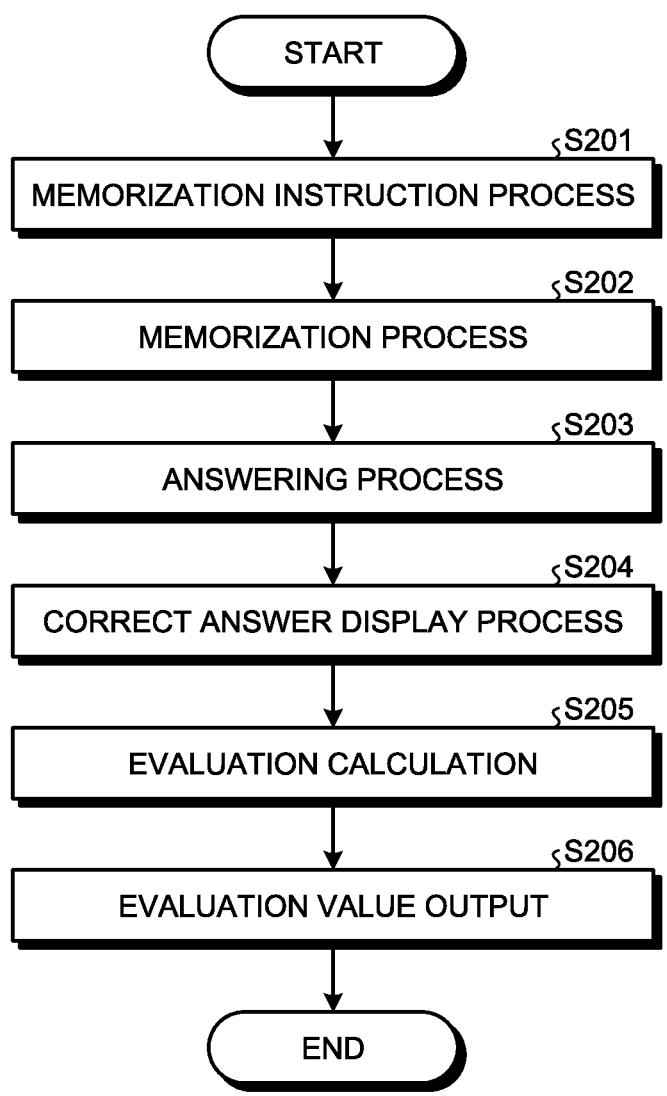
FIG. 24 is a flowchart illustrating a process in an evaluation method according to another example.

FIG. 24 is a flowchart illustrating a process in the evaluation method according to another example. As illustrated in FIG. 24, the display control unit 202 causes the instruction information 16 to be displayed so as to prompt the subject to memorize the type of food eaten by the bear among the five types of food (a memorization instruction process: Step S201).

Subsequently, in the first display operation, the display control unit 202 causes the display screen 101S to display the moving image in which the bear eats one type of food among the five types of food and prompts the subject to memorize it (a memorization process: Step S202).

Subsequently, in the second display operation, the display control unit 202 causes the instruction information 17 to be displayed so as to cause the subject to gaze at the type of food eaten by the bear among the five types of food while the five types of food are arranged in front of the bear (an answering process: Step S203).

Then, the display control unit 202 causes the image indicating the correct answer to the instruction information 17 to be displayed (a correct answer display process: Step S204).

Subsequently, the evaluating unit 224 calculates the evaluation value ANS based on the presence time data, the movement frequency data, the final area data, and the reaching time data obtained from the above-described processing result and obtains the evaluation data based on the evaluation value ANS (Step S205). Then, the output control unit 226 outputs the evaluation data obtained by the evaluating unit 224 (Step S206).

Figure 25:
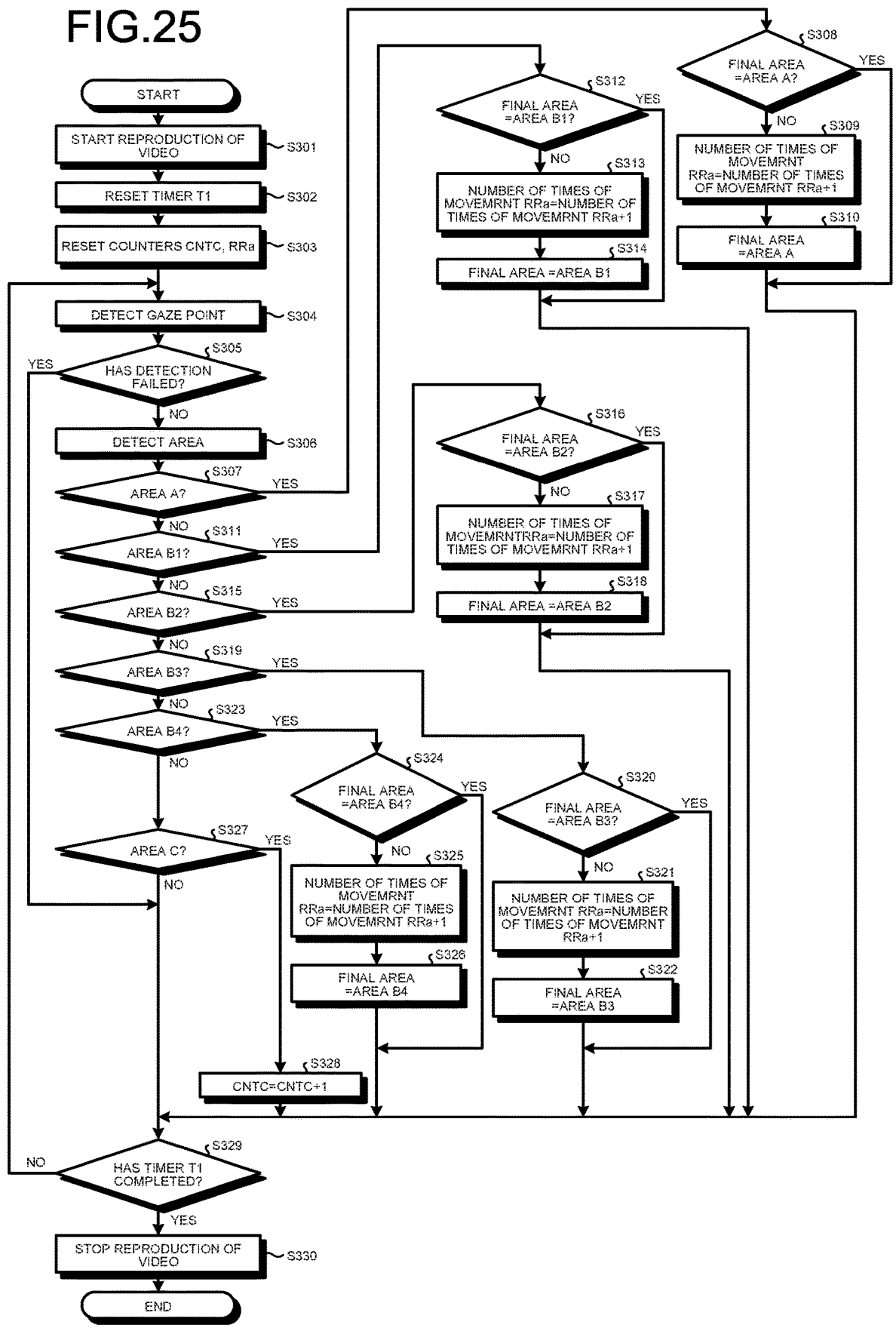
FIG. 25 is a flowchart illustrating a memorization instruction process.

FIG. 25 is a flowchart illustrating the memorization instruction process (Step S201). As illustrated in FIG. 25, during the memorization instruction process, the display control unit 202 starts the reproduction of a video (Step S301). After the waiting time for the video part has elapsed, the calculating unit 220 resets the timer T1 (Step S302) and resets count values CNTC and RRa of the counters (Step S303). The timer T1 is a timer for obtaining the end timing of a video of a memorization instruction process part in this video. The counter CNTC is to measure the count value CNTC indicating the presence time data of the gaze point P in the instruction area C. The counter RRa is a counter that counts the number of times of movement RRa indicating how many times the gaze point P has moved among the areas during the video reproduction period.

The gaze point detecting unit 214 detects the positional data of the gaze point of the subject on the display screen 101S of the display device 101 in every prescribed sampling period (e.g., 20 [msec]) while the video displayed by the display device 101 is presented to the subject (Step S304). When no positional data is detected (Yes at Step S305), the process starting from Step S329 described below is performed. When positional data is detected (No at Step S305), the determining unit 218 determines the area where the gaze point P is present based on the positional data (Step S306).

When it is determined that the gaze point P is present in the specific area A (Yes at Step S307), the calculating unit 220 determines whether the area where the gaze point P is present during the most recent detection, that is, the final area, is the specific area A (Step S308). When it is determined that the last area is the specific area A (Yes at Step S308), the calculating unit 220 skips the following Steps S309 and Step S310 and performs the operation at Step S329 described later. When it is determined that the final area is not the specific area A (No at Step S308), the calculating unit 220 increments by one the number of times of movement RRa indicating how many times the gaze point P has moved among the areas (Step S309) and changes the final area to the specific area A (Step S310). Then, the calculating unit 220 performs the process starting from Step S329 described later.

When it is determined that the gaze point P is not present in the specific area A (No at Step S307), the calculating unit 220 determines whether the gaze point P is present in the comparison area B1 (Step S311). When it is determined that the gaze point P is present in the comparison area B1 (Yes at Step S311), the calculating unit 220 determines whether the area where the gaze point P is present during the most recent detection, that is, the final area, is the comparison area B1 (Step S312). When it is determined that the final area is the comparison area B1 (Yes at Step S312), the calculating unit 220 skips the following Step S313 and Step S314 and performs the operation at Step S329 described later. When it is determined that the final area is not the comparison area B1 (No at Step S312), the calculating unit 220 increments by one the number of times of movement RRa indicating how many times the gaze point P has moved among the areas (Step S313) and changes the final area to the comparison area B1 (Step S314). Then, the calculating unit 220 performs the process starting from Step S329 described later.

When it is determined that the gaze point P is not present in the specific area B1 (No at Step S311), the calculating unit 220 determines whether the gaze point P is present in the comparison area B2 (Step S315). When it is determined that the gaze point P is present in the comparison area B2 (Yes at Step S315), the calculating unit 220 determines whether the area where the gaze point P is present during the most recent detection, that is, the final area, is the comparison area B2 (Step S316). When it is determined that the final area is the comparison area B2 (Yes at Step S316), the calculating unit 220 skips the following Step S317 and Step S318 and performs the operation at Step S329 described later. When it is determined that the final area is not the comparison area B2 (No at Step S316), the calculating unit 220 increments by one the number of times of movement RRa indicating how many times the gaze point P has moved among the areas (Step S317) and changes the final area to the comparison area B2 (Step S318). Then, the calculating unit 220 performs the process starting from Step S329 described later.

When it is determined that the gaze point P is not present in the specific area B2 (No at Step S315), the calculating unit 220 determines whether the gaze point P is present in the comparison area B3 (Step S319). When it is determined that the gaze point P is present in the comparison area B3 (Yes at Step S319), the calculating unit 220 determines whether the area where the gaze point P is present during the most recent detection, that is, the final area, is the comparison area B3 (Step S320). When it is determined that the final area is the comparison area B3 (Yes at Step S320), the calculating unit 220 skips the following Step S321 and Step S322 and performs the operation at Step S329 described later. When it is determined that the final area is not the comparison area B3 (No at Step S320), the calculating unit 220 increments by one the number of times of movement RRa indicating how many times the gaze point P has moved among the areas (Step S321) and changes the final area to the comparison area B3 (Step S322). Then, the calculating unit 220 performs the process starting from Step S329 described later.

When it is determined that the gaze point P is not present in the specific area B3 (No at Step S319), the calculating unit 220 determines whether the gaze point P is present in the comparison area B4 (Step S323). When it is determined that the gaze point P is present in the comparison area B4 (Yes at Step S323), the calculating unit 220 determines whether the area where the gaze point P is present during the most recent detection, that is, the final area, is the comparison area B4 (Step S324). When it is determined that the final area is the comparison area B4 (Yes at Step S324), the calculating unit 220 skips the following Step S325 and Step S326 and performs the operation at Step S329 described later. When it is determined that the final area is not the comparison area B4 (No at Step S324), the calculating unit 220 increments by one the number of times of movement RRa indicating how many times the gaze point P has moved among the areas (Step S325) and changes the final area to the comparison area B4 (Step S326). Then, the calculating unit 220 performs the process starting from Step S329 described later.

When it is determined that the gaze point P is not present in the specific area B4 (No at Step S323), the calculating unit 220 determines whether the gaze point P is present in the instruction area C (Step S327). When it is determined that the gaze point P is not present in the instruction area C (No at Step S327), the process starting from Step S329 described later is performed. When it is determined that the gaze point P is present in the instruction area C (Yes at Step S327), the calculating unit 220 increments by one the count value CNTC indicating the presence time data of the gaze point P in the instruction area C (Step S328). Then, the calculating unit 220 performs the process starting from Step S329 described later.

Subsequently, the calculating unit 220 determines whether the video reproduction completion time has reached, based on the detection result of the detection timer T1 (Step S329). When the calculating unit 220 determines that the video reproduction completion time has not reached (No at Step S329), the process starting from Step S304 described above is repeatedly performed.

When the calculating unit 220 determines that the video reproduction completion time has reached (Yes at Step S329), the display control unit 202 stops the reproduction of the video (Step S330). After the reproduction of the video is stopped, the memorization process (Step S202) is performed.

Figure 26:
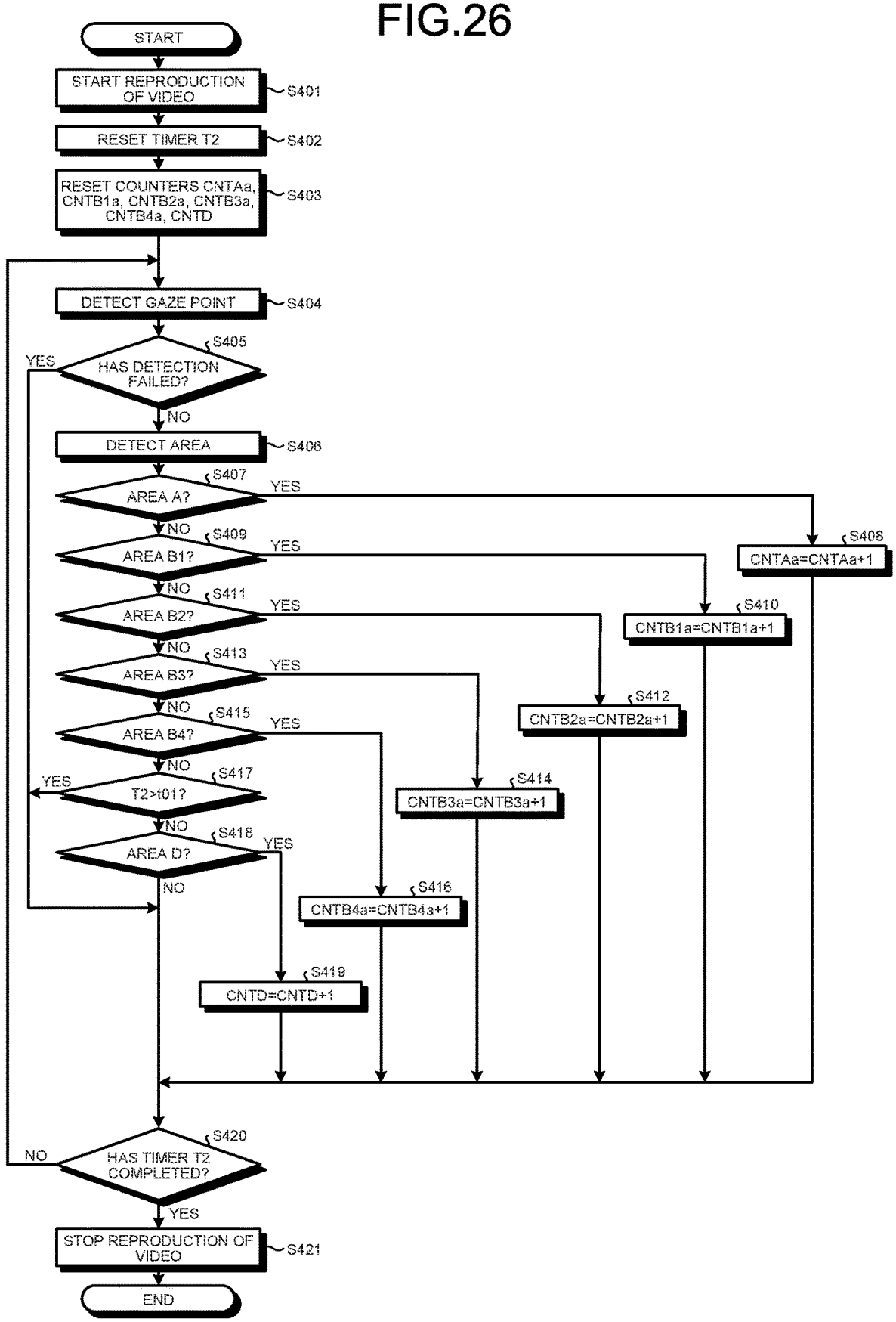
FIG. 26 is a flowchart illustrating a memorization process.

FIG. 26 is a flowchart illustrating the memorization process (Step S202). As illustrated in FIG. 26, in the memorization process, the display control unit 202 starts the reproduction of the video (Step S401). After the waiting time for the video part has elapsed, the calculating unit 220 resets a timer T2 (Step S402) and resets count values CNTAa, CNTB1a, CNTB2a, CNTB3a, CNTB4a, and CNTD of counters (Step S403). The timer T2 is a timer for obtaining the end timing of a video of a memorization process part in this video. The counter CNTAa is to measure the count value CNTAa indicating the presence time data of the gaze point P in the specific area A. The counters CNTB1a to CNTB4a are to measure the count values CNTB1a to CNTB4a indicating the presence time data of the gaze point P in the comparison areas B1 to B4. The counter CNTD is to measure the count value CNTD indicating the presence time data of the gaze point P in the movement area D.

The gaze point detecting unit 214 detects the positional data of the gaze point of the subject on the display screen 101S of the display device 101 in every prescribed sampling period (e.g., 20 [msec]) while the video displayed by the display device 101 is presented to the subject (Step S404). When no positional data is detected (Yes at Step S405), the process starting from Step S420 described below is performed. When positional data is detected (No at Step S405), the determining unit 218 determines the area where the gaze point P is present based on the positional data (Step S406).

When it is determined that the gaze point P is present in the specific area A (Yes at Step S407), the calculating unit 220 increments by one the count value CNTAa indicating the presence time data of the gaze point P in the specific area A (Step S408). Then, the calculating unit 220 performs the process starting from Step S420 described later.

When it is determined that the gaze point P is not present in the specific area A (No at Step S407), the calculating unit 220 determines whether the gaze point P is present in the comparison area B1 (Step S409). When it is determined that the gaze point P is present in the comparison area B1 (Yes at Step S409), the calculating unit 220 increments by one the count value CNTB1a indicating the presence time data of the gaze point P in the comparison area B1 (Step S410). Then, the calculating unit 220 performs the process starting from Step S420 described later.

When it is determined that the gaze point P is not present in the specific area B1 (No at Step S409), the calculating unit 220 determines whether the gaze point P is present in the comparison area B2 (Step S411). When it is determined that the gaze point P is present in the comparison area B2 (Yes at Step S411), the calculating unit 220 increments by one the count value CNTB2a indicating the presence time data of the gaze point P in the comparison area B2 (Step S412). Then, the calculating unit 220 performs the process starting from Step S420 described later.

When it is determined that the gaze point P is not present in the specific area B2 (No at Step S411), the calculating unit 220 determines whether the gaze point P is present in the comparison area B3 (Step S413). When it is determined that the gaze point P is present in the comparison area B3 (Yes at Step S413), the calculating unit 220 increments by one the count value CNTB3a indicating the presence time data of the gaze point P in the comparison area B3 (Step S414). Then, the calculating unit 220 performs the process starting from Step S420 described later.

When it is determined that the gaze point P is not present in the specific area B3 (No at Step S413), the calculating unit 220 determines whether the gaze point P is present in the comparison area B4 (Step S415). When it is determined that the gaze point P is present in the comparison area B4 (Yes at Step S415), the calculating unit 220 increments by one the count value CNTB4a indicating the presence time data of the gaze point P in the comparison area B4 (Step S416). Then, the calculating unit 220 performs the process starting from Step S420 described later.

When it is determined that the gaze point P is not present in the specific area B4 (No at Step S415), the calculating unit 220 determines whether the value of the timer T2 exceeds a predetermined time t01 (Step S417). The predetermined time t01 is the time when the orange in the bear's mouth becomes invisible after the mouth is closed. When the value of the timer T2 exceeds the predetermined time t01 (Yes at Step S417), the calculating unit 220 skips the operation at Step S418 and performs the process starting from Step S420 described later. When the value of the timer T2 does not exceed the predetermined time t01 (No at Step S417), the calculating unit 220 determines whether the gaze point P is present in the movement area D (Step S418). When it is determined that the gaze point P is not present in the movement area D (No at Step S418), the process starting from Step S420 described later is performed. When it is determined that the gaze point P is present in the movement area D (Yes at Step S418), the calculating unit 220 increments by one the count value CNTD indicating the presence time data of the gaze point P in the movement area D (Step S419). Then, the calculating unit 220 performs the process starting from Step S420 described later.

Then, the calculating unit 220 determines whether the video reproduction completion time has reached, based on the detection result of the detection timer T2 (Step S420). When the calculating unit 220 determines that the video reproduction completion time has not reached (No at Step S420), the process starting from Step S404 described above is repeatedly performed.

When the calculating unit 220 determines that the video reproduction completion time has reached (Yes at Step S420), the display control unit 202 stops the reproduction of the video (Step S421). After the reproduction of the video is stopped, the answering process (Step S203) is performed.

Figure 27:
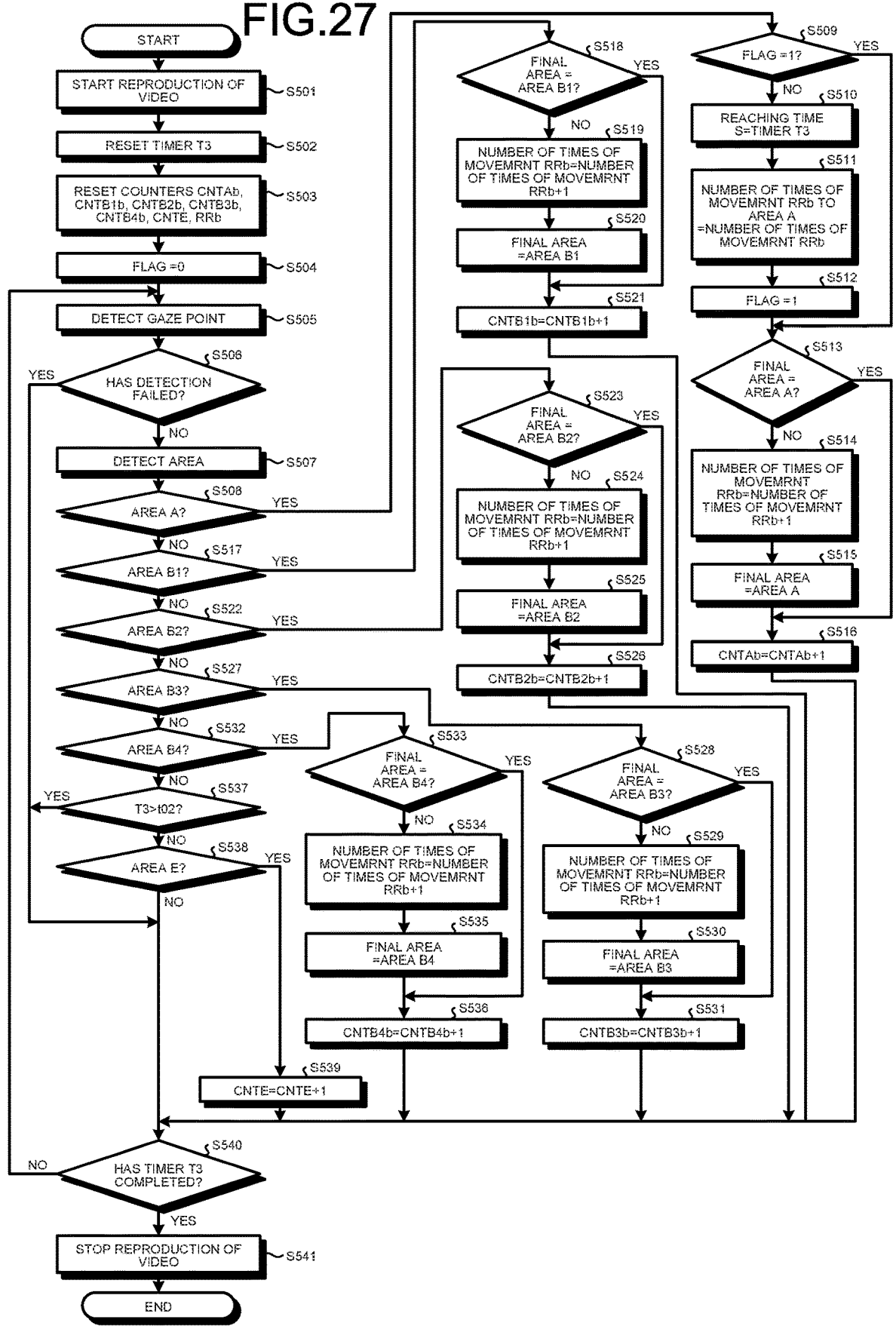
FIG. 27 is a flowchart illustrating an answering process.

FIG. 27 is a flowchart illustrating the answering process (Step S203). As illustrated in FIG. 27, in the answering process, the display control unit 202 starts the reproduction of the video (Step S501). After the waiting time for the video part has elapsed, the calculating unit 220 resets a timer T3 (Step S502), resets count values CNTAb, CNTB1b, CNTB2b, CNTB3b, CNTB4b, CNTE, RRb of counters (Step S503), and sets a flag value to 0 (Step S504). The timer T3 is a timer for obtaining the end timing of a video of an answering process part in this video. The counter CNTAb is to measure the count value CNTAb indicating the presence time data of the gaze point P in the specific area A. The counters CNTB1b to CNTB4b are to measure the count values CNTB1b to CNTB4b indicating the presence time data of the gaze point P in the comparison areas B1 to B4. The counter CNTE is to measure the count value CNTE indicating the presence time data of the gaze point P in the instruction area E. The counter RRb is a counter that counts the number of times of movement RRb indicating how many times the gaze point P has moved among the areas.

The gaze point detecting unit 214 detects the positional data of the gaze point of the subject on the display screen 101S of the display device 101 in every prescribed sampling period (e.g., 20 [msec]) while the video displayed by the display device 101 is presented to the subject (Step S505). When positional data is detected (No at Step S506), the determining unit 218 determines the area where the gaze point P is present based on the positional data (Step S507).

When it is determined that the gaze point P is present in the specific area A (Yes at Step S508), the calculating unit 220 determines whether the flag value is 1, that is, whether the gaze point P has first reached the specific area A (1: has reached, 0: has not reached) (Step S509). When the flag value is 1 (Yes at Step S509), the calculating unit 220 skips the following Step S510 to Step S512 and performs the operation at Step S513 described later.

When the flag value is not 1, that is, when the gaze point P has not first reached the specific area A (No at Step S509), the calculating unit 220 extracts the measurement result of the timer T3 as the reaching time data (Step S510). The calculating unit 220 stores, in the storage unit 222, the movement frequency data indicating how many times the gaze point P has moved among the areas before reaching the specific area A (Step S511). Then, the calculating unit 220 changes the flag value to 1 (Step S512).

Subsequently, the calculating unit 220 determines whether the area where the gaze point P is present during the most recent detection, that is, the final area, is the specific area A (Step S513). When it is determined that the final area is the specific area A (Yes at Step S513), the calculating unit 220 skips the following Step S514 and Step S515 and performs the operation at Step S516 described later. When it is determined that the final area is not the specific area A (No at Step S513), the calculating unit 220 increments by one the number of times of movement indicating how many times the gaze point P has moved among the areas (Step S514) and changes the final area to the specific area A (Step S515). The calculating unit 220 increments by one the count value CNTAb indicating the presence time data of the gaze point P in the specific area A (Step S516). Then, the calculating unit 220 performs the process starting from Step S540 described later.

When it is determined that the gaze point P is not present in the specific area A (No at Step S508), the calculating unit 220 determines whether the gaze point P is present in the comparison area B1 (Step S517). When it is determined that the gaze point P is present in the comparison area B1 (Yes at Step S517), the calculating unit 220 determines whether the area where the gaze point P is present during the most recent detection, that is, the final area, is the comparison area B1 (Step S518). When it is determined that the final area is the comparison area B1 (Yes at Step S518), the calculating unit 220 skips the following Step S519 and Step S520 and performs the operation at Step S521 described later. When it is determined that the final area is not the comparison area B1 (No at Step S518), the calculating unit 220 increments by one the number of times of movement indicating how many times the gaze point P has moved among the areas (Step S519) and changes the final area to the comparison area B1 (Step S520). The calculating unit 220 increments by one the count value CNTB1*b* indicating the presence time data of the gaze point P in the comparison area B1 (Step S521). Then, the calculating unit 220 performs the process starting from Step S540 described later.

When it is determined that the gaze point P is not present in the comparison area B1 (No at Step S517), the calculating unit 220 determines whether the gaze point P is present in the comparison area B2 (Step S522). When it is determined that the gaze point P is present in the comparison area B2 (Yes at Step S522), the calculating unit 220 determines whether the area where the gaze point P is present during the most recent detection, that is, the final area, is the comparison area B2 (Step S523). When it is determined that the final area is the comparison area B2 (Yes at Step S523), the calculating unit 220 skips the following Step S524 and Step S525 and performs the process at Step S526 described below. When it is determined that the final area is not the comparison area B2 (No at Step S523), the calculating unit 220 increments by one the number of times of movement indicating how many times the gaze point P has moved among the areas (Step S524) and changes the final area to the comparison area B2 (Step S525). The calculating unit 220 increments by one the count value CNTB2*b* indicating the presence time data of the gaze point P in the comparison area B2 (Step S526). Then, the calculating unit 220 performs the process starting from Step S540 described later.

When it is determined that the gaze point P is not present in the comparison area B2 (No at Step S522), the calculating unit 220 determines whether the gaze point P is present in the comparison area B3 (Step S527). When it is determined that the gaze point P is present in the comparison area B3 (Yes at Step S527), the calculating unit 220 determines whether the area where the gaze point P is present during the most recent detection, that is, the final area, is the comparison area B3 (Step S528). When it is determined that the final area is the comparison area B3 (Yes at Step S528), the calculating unit 220 skips the following Step S529 and Step S530 and performs the operation at Step S531 described below. When it is determined that the final area is not the comparison area B3 (No at Step S528), the calculating unit 220 increments by one the number of times of movement indicating how many times the gaze point P has moved among the areas (Step S529) and changes the final area to the comparison area B3 (Step S530). The calculating unit 220 increments by one the count value CNTB3*b* indicating the presence time data of the gaze point P in the comparison area B3 (Step S531). Then, the calculating unit 220 performs the process starting from Step S540 described later.

When it is determined that the gaze point P is not present in the comparison area B3 (No at Step S527), the calculating unit 220 determines whether the gaze point P is present in the comparison area B4 (Step S532). When it is determined that the gaze point P is present in the comparison area B4 (Yes at Step S532), the calculating unit 220 determines whether the area where the gaze point P is present during the most recent detection, that is, the final area, is the comparison area B4 (Step S533). When it is determined that the final area is the comparison area B4 (Yes at Step S533), the calculating unit 220 skips the following Step S534 and Step S535 and performs the operation at Step S536 described later. When it is determined that the final area is not the comparison area B4 (No at Step S533), the calculating unit 220 increments by one the number of times of movement indicating how many times the gaze point P has moved among the areas (Step S534) and changes the final area to the comparison area B4 (Step S535). The calculating unit 220 increments by one the count value CNTB4*b* indicating the presence time data of the gaze point P in the comparison area B4 (Step S536). Then, the calculating unit 220 performs the operation starting from Step S540 described later.

When it is determined that the gaze point P is not present in the comparison area B4 (No at Step S532), the calculating unit 220 determines whether the value of the timer T3 exceeds a predetermined time t02 (Step S537). The predetermined time t02 is a time when the display of the instruction information 17 is deleted. When the value of the timer T3 exceeds the predetermined time t02 (Yes at Step S537), the calculating unit 220 skips the operation at Step S538 and performs the process starting from Step S540 described later. When the value of the timer T3 does not exceed the predetermined time t02 (No at Step S537), the calculating unit 220 determines whether the gaze point P is present in the instruction area E (Step S538). When it is determined that the gaze point P is present in the instruction area E (Yes at Step S538), the calculating unit 220 increments by one the count value CNTE indicating the presence time data of the gaze point P in the instruction area E (Step S539). Then, the calculating unit 220 performs the process starting from Step S540 described later.

Then, the calculating unit 220 determines whether the video reproduction completion time has reached, based on the detection result of the detection timer T3 (Step S540). When the calculating unit 220 determines that the video reproduction completion time has not reached (No at Step S540), the process starting from Step S505 described above is repeatedly performed.

When the calculating unit 220 determines that the video reproduction completion time has reached (Yes at Step S540), the display control unit 202 stops the reproduction of the video (Step S541). After the reproduction of the video is stopped, the evaluation calculation (Step S205) and the evaluation value output (Step S206) are performed.

For the evaluation calculation, the evaluation value ANS is, for example, represented as follows:

$$ANS = K11 \cdot RRa + K12 \cdot CNTC + K13 \cdot CNTAa + K14 \cdot CNTB1a + K15 \cdot CNTB2a + K16 \cdot CNTB3a + K17 \cdot CNTB4a + K18 \cdot CNTD + K19 \cdot CNTAb + K20 \cdot CNTB1b + K21 \cdot CNTB2b + K22 \cdot CNTB3b + K23 \cdot CNTB4b + K24 \cdot CNTE + K25 \cdot RRb$$

where K11 to K25 are constants for weighting. The constants K11 to K25 may be set as appropriate.

The higher the tendency to look closely at the object, the higher the numerical value of RRa. In this case, by setting K11 to a negative coefficient, the value of the evaluation value ANS is decreased with an increase in the value of RRa.

The higher the tendency to look closely at the instruction text, the higher the numerical value of CNTC. In this case, by setting K12 to a negative coefficient, the value of the evaluation value ANS is decreased with an increase in the value of CNTC.

The higher the tendency to closely look at the orange eaten by the bear, the higher the numerical value of CNTAa. In this case, by setting K13 to a negative coefficient, the value of the evaluation value ANS is decreased with an increase in the value of CNTA.

The higher the tendency to look aimlessly at the objects other than the orange eaten by the bear, the higher the numerical values of CNTB1*a* to CNTB4*a*. In this case, by setting K14 to K17 to positive coefficients, the value of the evaluation value ANS is increased with an increase in the values of CNTB1*a* to CNTB4*a*.

The higher the tendency to look closely at the object, the higher the numerical value of CNTD. The tendency to simply look at a moving object also causes an increase in the numeric value. In this case, K18 may be set to a positive coefficient and, for example, may have a low value as compared with the other coefficients.

The closer the look one takes at the orange that is a correct answer, the higher the numerical value of CNTAb. In this case, by setting K19 to a negative coefficient and setting the absolute value thereof to be larger than those of the other coefficients, the value of the evaluation value ANS is significantly decreased with an increase in the value of CNTAb.

The closer the look one takes at the food that is not a correct answer, the higher the numerical values of CNTB1$b$ to CNTB4$b$. In this case, by setting K20 to K23 to positive coefficients and setting the absolute values thereof to be larger than those of the other coefficients, the value of the evaluation value ANS is significantly increased with an increase in the values of CNTB1$b$ to CNTB4$b$.

The higher the tendency to look closely at the instruction information 17, the higher the numerical value of CNTE. In this case, by setting K24 to a negative coefficient, the value of the evaluation value ANS is decreased with an increase in the value of CNTE.

The higher the tendency to vacillate over the choice of a correct answer, the higher the numerical value of RRb. In this case, by setting K25 to a positive coefficient, the value of the evaluation value ANS is increased with an increase in the value of RRb.

The evaluating unit 224 may determine whether the evaluation value ANS is greater than a predetermined value so as to obtain the evaluation data. For example, when the evaluation value ANS is equal to or greater than the predetermined value, it may be evaluated that the subject is likely to have cognitive dysfunction and brain dysfunction. When the evaluation value ANS is less than the predetermined value, it may be evaluated that the subject is unlikely to have cognitive dysfunction and brain dysfunction.

The evaluating unit 224 may obtain the evaluation value of the subject based on at least one data item included in the above-described gaze point data. For example, when the presence time data CNTAb of the specific area A is equal to or greater than a predetermined value, the evaluating unit 224 may evaluate that the subject is unlikely to have cognitive dysfunction and brain dysfunction. When the ratio of the presence time data CNTAb of the specific area A to the total of the presence time data CNTB1$b$ to CNTB4$b$ of the comparison areas B1 to B4 (the ratio of the gazing rates of the specific area A and the comparison areas B1 to B4) is equal to or greater than a predetermined value, the evaluating unit 224 may evaluate that the subject is unlikely to have cognitive dysfunction and brain dysfunction. When the ratio of the presence time data CNTAb of the specific area A to the overall gazing time (the ratio of the gazing time of the specific area A to the total gazing time) is equal to or greater than a predetermined value, the evaluating unit 224 may evaluate that the subject is unlikely to have cognitive dysfunction and brain dysfunction. The evaluating unit 224 may evaluate that the subject is unlikely to have cognitive dysfunction and brain dysfunction when the final area is the specific area A; and evaluate that the subject is likely to have cognitive dysfunction and brain dysfunction when the final area is any one of the comparison areas B1 to B4.

Figure 28:
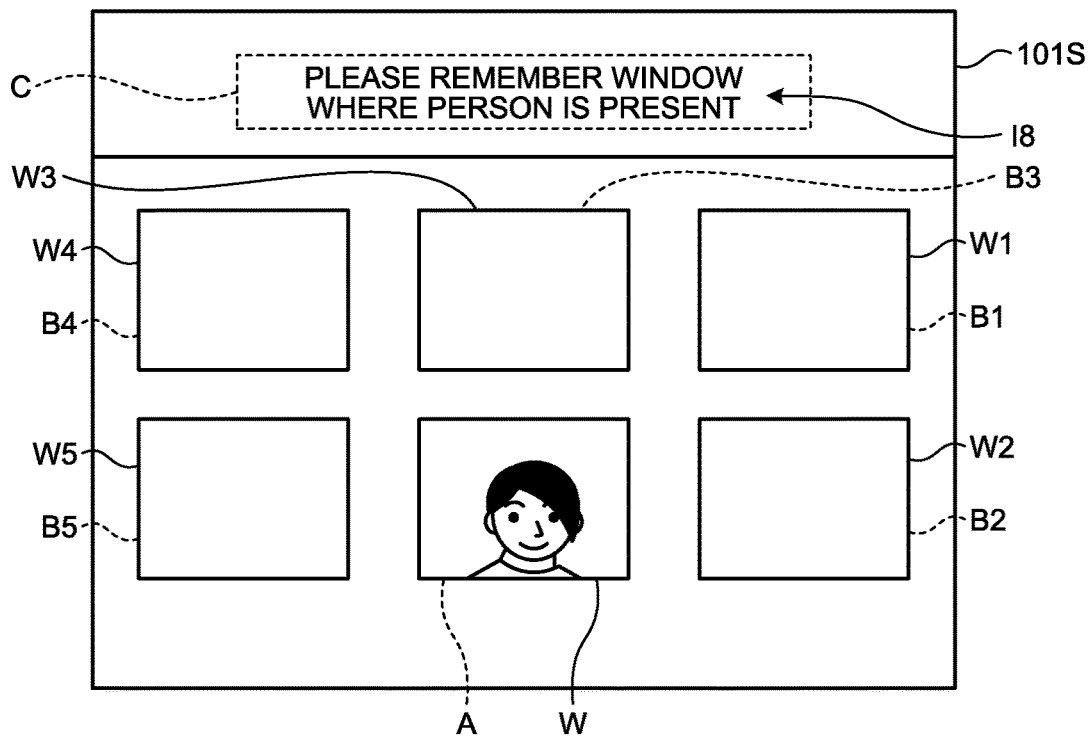
FIG. 28 is a diagram illustrating an example of a series of evaluation images displayed on the display screen.
Figure 29:
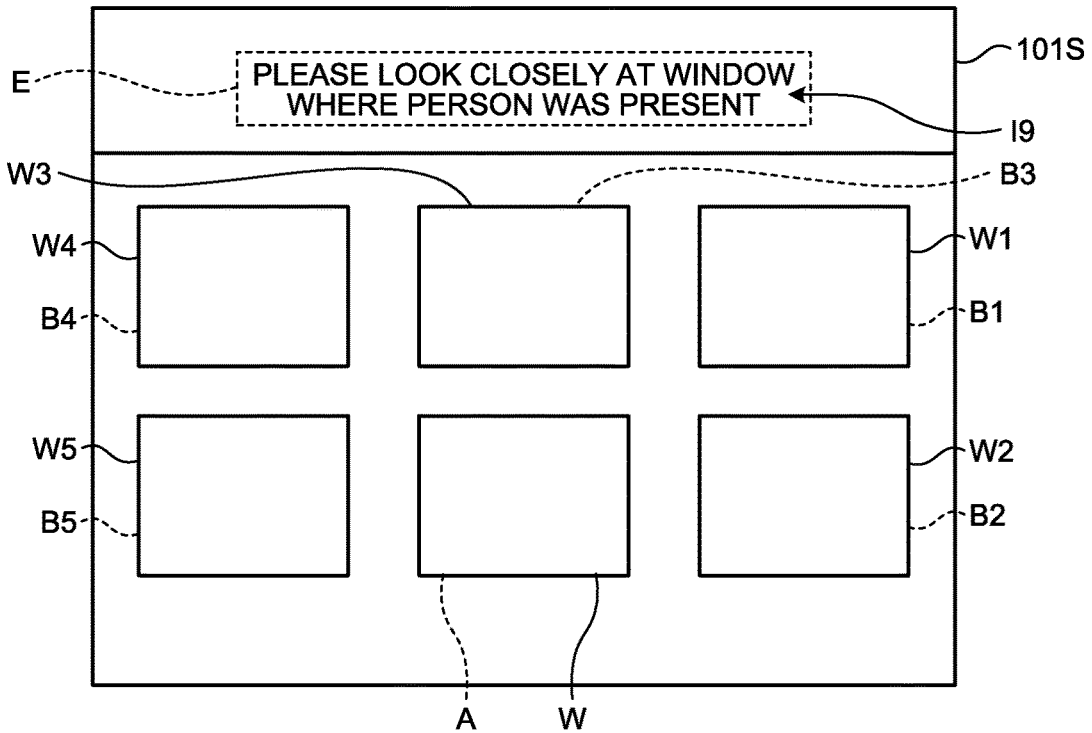
FIG. 29 is a diagram illustrating an example of a series of evaluation images displayed on the display screen.
Figure 30:
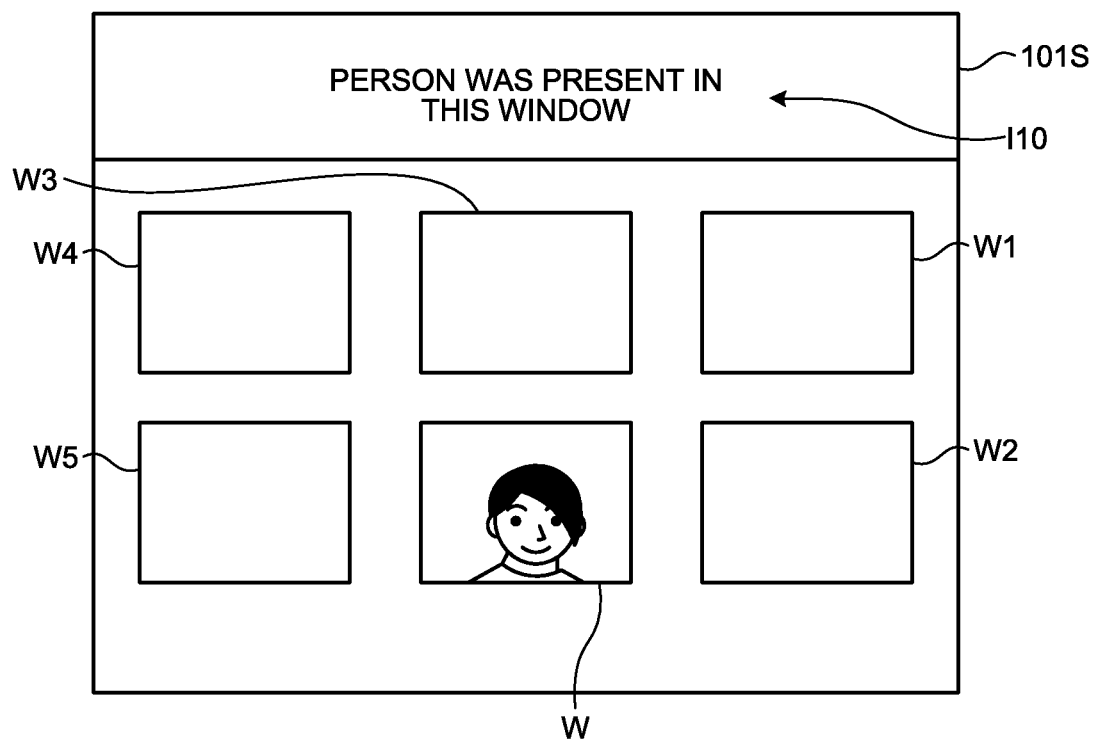
FIG. 30 is a diagram illustrating an example of a series of evaluation images displayed on the display screen.

FIG. 28 to FIG. 30 are diagrams illustrating another example of the series of evaluation images displayed on the display screen 101S. As illustrated in FIG. 28, in the first display operation, the display control unit 202 first causes the display screen 101S to display the image in which a person puts his face through a window out of multiple (e.g., six) windows. The six types of windows correspond to objects W, W1 to W5. The display control unit 202 causes instruction information 18 to be displayed so as to prompt the subject to memorize, out of the six windows, a window through which the person puts his face. In this case, among the objects W, W1 to W5, the window through which the person puts his face is the specific object W. The windows other than the window through which the person puts his face are the comparison objects W1 to W5.

As illustrated in FIG. 28, the area setting unit 216 sets the specific area A corresponding to the specific object W and sets the comparison areas B1 to B5 corresponding to the comparison objects W1 to W5. The area setting unit 216 sets the instruction area C corresponding to the instruction information 18. The area setting unit 216 sets, for example, a rectangular area corresponding to the specific object W as the specific area A. In FIG. 28, as the specific object W is a rectangular window, the specific area A may be set so as to be overlapped with the outline of the window. Similarly, the area setting unit 216 may set the comparison areas B1 to B5 so as to be overlapped with, for example, the outlines of the windows that are the comparison objects W1 to W5. The area setting unit 216 sets a rectangular area including the instruction information 18 as the instruction area C. The shapes of the specific area A, the comparison areas B1 to B5, and the instruction area C are not limited to a rectangular shape and may be other shapes such as a circle, an ellipse, or a polygon. In this case, the area setting unit 216 sets the specific area A, the comparison areas B1 to B5, and the instruction area C so as not to be overlapped with each other. The display control unit 202 and the area setting unit 216 maintain this state for a predetermined period of time. Specifically, the display control unit 202 causes the display screen 101S to display the specific object W and the comparison objects W1 to W5 for a predetermined period of time. The area setting unit 216 sets the specific area A corresponding to the specific object W for a predetermined period of time and sets the comparison areas B1 to B5 corresponding to the comparison objects W1 to W5 for a predetermined period of time. In this predetermined period of time, the subject is prompted to gaze at the specific object W and the comparison objects W1 to W5.

After the above-described display is given for a predetermined period of time, as illustrated in FIG. 29, the display control unit 202 deletes the image of the person from the window that is the specific object W. In this manner, the display control unit 202 changes the display form of the specific object W. Subsequently, in the second display operation, instruction information 19 is displayed so as to cause the subject to gaze at the window through which the person put his face out of the six windows. The area setting unit 216 sets the specific area A corresponding to the specific object W and sets the comparison areas B1 to B5 corresponding to the comparison objects W1 to W5 continuously from the state illustrated in FIG. 28. The area setting unit 216 sets the instruction area E corresponding to the instruction information 19. The shapes of the specific area A, the comparison areas B1 to B5, and the instruction area E are not limited to a rectangular shape and may be other shapes such as a circle, an ellipse, or a polygon. In this case, the area setting unit 216 sets the specific area A, the comparison areas B1 to B5, and the instruction area E so as not to be overlapped with each other.

After the second display operation is performed for a predetermined period of time, the display control unit 202 may cause the image indicating the correct answer to the instruction information 19 to be displayed as illustrated in FIG. 30. In FIG. 30, for example, the person puts his face again through the window corresponding to the specific object W, and instruction information I10 indicating that the window is the correct answer is displayed. As the image in FIG. 30 is displayed, it is possible to make the subject clearly know the correct answer. In a case where the image indicating the correct answer is displayed, the area setting unit 216 may cancel the specific area A, the comparison areas B1 to B5, and the instruction area E.

As described above, the evaluation apparatus 100 according to the above-described embodiment includes: the display screen 101S; the gaze point detecting unit 214 that detects the position of the gaze point of the subject observing the display screen 101S; the display control unit 202 that causes the display screen 101S to display the image including the specific object and a comparison object different from the specific object; the area setting unit 216 that sets the specific area corresponding to the specific object and the comparison area corresponding to the comparison object; the determining unit 218 that, based on the position of the gaze point, determines whether the gaze point is present in the specific area and the comparison area during the period in which the image is displayed; the calculating unit 220 that calculates the gaze point data indicating the progress of movement of the gaze point, based on the determination result of the determining unit 218; and the evaluating unit 224 that obtains the evaluation data of the subject based on the gaze point data.

The evaluation method according to the above-described embodiment includes: detecting the position of the gaze point of the subject observing the display screen 101S; causing the display screen 101S to display the image including the specific object and the comparison object different from the specific object; setting the specific area corresponding to the specific object and the comparison area corresponding to the comparison object; determining, based on the position of the gaze point, whether the gaze point is present in the specific area and the comparison area during the display period in which the display screen displays the image; calculating the gaze point data indicating the progress of movement of the gaze point during the display period based on the determination result; and obtaining the evaluation data of the subject based on the gaze point data.

The evaluation program according to the above-described embodiment causes a computer to execute: a process of detecting the position of the gaze point of the subject observing the display screen 101S; the process of causing the display screen 101S to display the image including the specific object and the comparison object different from the specific object; a process of setting the specific area corresponding to the specific object and the comparison area corresponding to the comparison object; a process of determining, based on the position of the gaze point, whether the gaze point is present in the specific area and the comparison area during the display period in which the display screen displays the image; a process of calculating the gaze point data indicating the progress of movement of the gaze point during the display period based on the determination result; and a process of obtaining the evaluation data of the subject based on the gaze point data.

Therefore, in a case where the display form of the specific object is not changed or in a case where the display form of the specific object is changed during the first display operation, it is possible to obtain the evaluation data of the subject based on the progress of movement of the gaze point during the display period. As described above, by virtue of the variety of display forms of the specific object, the accidentalness may be further reduced, and the memory ability of the subject may be evaluated with high accuracy. Thus, the evaluation apparatus 100 may evaluate the subject with high accuracy.

According to one aspect of the present disclosure, it is possible to provide an evaluation apparatus, an evaluation method, and an evaluation program with which it is possible to evaluate cognitive dysfunction and brain dysfunction with high accuracy.

What is claimed is:

1. An evaluation apparatus comprising:
a display screen; and
an arithmetic processing device includes a microprocessor, which executes processes of a gaze point detecting unit, a display control unit, an area setting unit, a determining unit, a calculating unit, and an evaluating unit, wherein,
the gaze point detecting unit detects a position of a gaze point of a subject observing the display screen;
the display control unit causes the display screen to display an image including a specific object and a comparison object different from the specific object, and an instruction information instructing or prompting a user to memorize the specific object;
the area setting unit sets a specific area corresponding to the specific object, a comparison area corresponding to the comparison object, movement area corresponding to the area where a display form of the specific object is changed, and an instruction area corresponding to the instruction information;
the determining unit determines, based on the position of the gaze point, whether the gaze point is present in the specific area, whether the gaze point is in the comparison area, whether the gaze point is presented in the movement area, whether the gaze point is present in the instruction area, during a display period in which the image is displayed on the display screen;
the calculating unit calculates gaze point data based on a determination result of the determining unit; and
the evaluating unit obtains evaluation data of the subject based on the gaze point data, wherein
the display control unit performs a first display operation to change a display form of the specific object during a period in which the specific object and the comparison object are displayed on the display screen and then performs a second display operation to display the specific object in the display form before it was changed in the first display operation and the comparison object on the display screen, and
the display control unit, in the second display operation, causes instruction to be displayed so as to prompt the subject to memorize the specific object whose display form was changed in the first display operation,
and the evaluating unit calculates an evaluation data such that an evaluation value is smaller when presence time of the gaze point in the specific area is longer, the evaluation value is larger when presence time of the gaze point in the comparison area is longer, the evaluation value is larger when presence time of the gaze point in the movement area is longer, and the evaluation time is smaller when presence time of the gaze point in the instruction area is longer so as to evaluate cognitive dysfunction and brain dysfunction of the subject.

2. The evaluation apparatus according to claim 1, wherein the operation to change the display form of the specific object in the first display operation includes an operation to cause at least part of the specific object not to be displayed.

3. The evaluation apparatus according to claim 1, wherein the evaluating unit is configured to apply a weight to at least one data item included in the gaze point data to obtain the evaluation data.

4. An evaluation method comprising:
  causing a display screen to display an image including a specific object and a comparison object different from the specific object, and an instruction information instructing or prompting a user to memorize the specific object;
  setting a specific area corresponding to the specific object, a comparison area corresponding to the comparison object, a movement area corresponding to the area where a display form of the specific object is changed, and an instruction area corresponding to the instruction information;
  detecting a position of a gaze point of a subject observing the display screen;
  determining, based on the position of the gaze point, whether the gaze point is present in the specific area, whether the gaze point is present in the comparison area, whether the gaze point is presented in the movement area, whether the gaze point is presented in the instruction area, during a display period in which the display screen displays the image;
  calculating gaze point data during the display period based on the determination result;
  obtaining evaluation data of the subject based on the gaze point data;
  performing a first display operation to change a display form of the specific object during a period in which the specific object and the comparison object are displayed on the display screen, and then performing a second display operation to display the specific object in the display form before it was changed in the first display operation and the comparison object on the display screen; and
  in the second display operation, causing instruction to be displayed so as to prompt the subject to memorize the specific object whose display form was changed in the first display operation,
  and calculating an evaluation data such that an evaluation value is smaller when presence time of the gaze point in the specific area is longer, the evaluation value is larger when presence time of the gaze point in the comparison area is longer, the evaluation value is larger when presence time of the gaze point in the movement area is longer, and the evaluation time is smaller when presence time of the gaze point in the instruction area is longer so as to evaluate cognitive dysfunction and brain dysfunction of the subject.

5. A non-transitory storage medium that stores a computer program configured to cause a computer to execute:
  a process of causing a display screen to display an image including a specific object and a comparison object different from the specific object, and an instruction information instructing or prompting a user to memorize the specific;
  a process of setting a specific area corresponding to the specific object, a comparison area corresponding to the comparison object, a movement area corresponding to the area where a display form of the specific object is changed, and an instruction area corresponding to the instruction information;
  a process of detecting a position of a gaze point of a subject observing the display screen;
  a process of determining, based on the position of the gaze point, whether the gaze point is present in the specific area, whether the gaze point is present in the comparison area, whether the gaze point is presented in the movement area, whether the gaze point is presented in the instruction area, during a display period in which the display screen displays the image;
  a process of calculating gaze point data during the display period based on the determination result;
  a process of obtaining evaluation data of the subject based on the gaze point data;
  a process of performing a first display operation to change a display form of the specific object during a period in which the specific object and the comparison object are displayed on the display screen, and then performing a second display operation to display the specific object in the display form before it was changed in the first display operation and the comparison object on the display screen; and
  a process, in the second display operation, of causing instruction to be displayed so as to prompt the subject to memorize the specific object that changes in the display form in the first display operation
  and calculating an evaluation data such that an evaluation value is smaller when presence time of the gaze point in the specific area is longer, the evaluation value is larger when presence time of the gaze point in the comparison area is longer, the evaluation value is larger when presence time of the gaze point in the movement area is longer, and the evaluation time is smaller when presence time of the gaze point in the instruction area is longer so as to evaluate cognitive dysfunction and brain dysfunction of the subject.

\* \* \* \* \*